(12) United States Patent
Johnston

(10) Patent No.: US 11,185,338 B2
(45) Date of Patent: Nov. 30, 2021

(54) COMPRESSION CUFF

(71) Applicant: Covidien LP, Mansfield, MA (US)

(72) Inventor: Thomas M. Johnston, Westborough, MA (US)

(73) Assignee: Covidien LP, Mansfield, MA (US)

( * ) Notice: Subject to any disclaimer, the term of this patent is extended or adjusted under 35 U.S.C. 154(b) by 169 days.

(21) Appl. No.: 16/551,515

(22) Filed: Aug. 26, 2019

(65) Prior Publication Data
US 2021/0059687 A1 Mar. 4, 2021

(51) Int. Cl.
*A61B 17/132* (2006.01)
*A61B 8/08* (2006.01)
*A61B 90/00* (2016.01)

(52) U.S. Cl.
CPC ........ *A61B 17/1322* (2013.01); *A61B 8/0891* (2013.01); *A61B 2090/395* (2016.02)

(58) Field of Classification Search
CPC .............. A61B 17/132; A61B 17/1322; A61B 17/1325; A61B 17/135
See application file for complete search history.

(56) References Cited

U.S. PATENT DOCUMENTS

| | | |
|---|---|---|
| 4,597,384 A | 7/1986 | Whitney |
| 4,760,846 A | 8/1988 | Mers Kelly et al. |
| 5,254,087 A | 10/1993 | McEwen |
| 5,799,650 A | 9/1998 | Harris |
| 5,916,183 A * | 6/1999 | Reid .................. A61F 5/05858 601/134 |
| 6,605,103 B2 | 8/2003 | Hovanes et al. |
| 6,892,733 B2 | 5/2005 | Clinton |
| 7,758,607 B2 | 7/2010 | McEwen et al. |
| 7,771,453 B2 | 8/2010 | McEwen et al. |
| 7,892,253 B2 | 2/2011 | Esposito et al. |

(Continued)

FOREIGN PATENT DOCUMENTS

| | | |
|---|---|---|
| KR | 20140121247 A | 10/2014 |
| WO | 9625108 A1 | 8/1996 |
| WO | 2006/053920 A3 | 5/2006 |

OTHER PUBLICATIONS

EP20192003, Extended European Search Report, dated Sep. 29, 2020, 11pages.

*Primary Examiner* — Ryan J. Severson
(74) *Attorney, Agent, or Firm* — Shumaker & Sieffert, P.A.

(57) ABSTRACT

Devices, assemblies, systems, and techniques described herein may facilitate the closure of hollow anatomical structures (e.g., veins) with adhesive delivered within the hollow anatomical structure. For example, a medical assembly may include a plurality of medial compression members extending from a central body in a first direction, each medial compression member of the plurality of medial compression members comprising a first attachment element, and a plurality of lateral compression members extending from the central body in a second direction different than the first direction, each lateral compression member of the plurality of lateral compression members comprising a second attachment element. Each first attachment mechanism may be configured to attach to the respective second attachment element to create a respective loop configuration with a respective medial compression member and lateral compression member pair to compress a portion of the limb of the patient.

20 Claims, 12 Drawing Sheets

(56) References Cited

U.S. PATENT DOCUMENTS

| | | | |
|---|---|---|---|
| 7,947,862 B2 | 5/2011 | Livorsi | |
| 8,048,105 B2 | 11/2011 | McEwen et al. | |
| 8,366,740 B2 | 2/2013 | McEwen. et al. | |
| 8,475,492 B2 | 7/2013 | Raabe et al. | |
| 8,617,144 B2 * | 12/2013 | Ravikumar | A61B 17/135 606/1 |
| 8,663,144 B2 | 3/2014 | Farrow et al. | |
| 8,864,741 B2 | 10/2014 | Lilley | |
| 9,358,146 B2 | 6/2016 | Thorsteindottir et al. | |
| 10,470,778 B2 * | 11/2019 | Corrigan, Jr. | A61B 8/06 |
| 10,779,994 B2 * | 9/2020 | Hitschmann | A61F 13/085 |
| 2004/0193084 A1 | 9/2004 | Ravikumar | |
| 2005/0113798 A1 | 5/2005 | Slater et al. | |
| 2006/0052823 A1 | 3/2006 | Mirizzi et al. | |
| 2006/0149218 A1 | 7/2006 | Slater et al. | |
| 2008/0275499 A1 | 11/2008 | Brackett et al. | |
| 2012/0022422 A1 | 1/2012 | Ravikumar | |
| 2013/0190806 A1 | 7/2013 | McEwen et al. | |
| 2013/0282046 A1 | 10/2013 | Ravikumar | |
| 2016/0120729 A1 | 5/2016 | Ankrum et al. | |
| 2016/0354090 A1 | 12/2016 | Corrigan, Jr. | |
| 2017/0112504 A1 | 4/2017 | McEwen et al. | |
| 2018/0221213 A1 | 4/2018 | Hitschmann et al. | |
| 2020/0029974 A1 * | 1/2020 | Corrigan, Jr. | A61B 8/4227 |
| 2021/0059687 A1 * | 3/2021 | Johnston | A61B 8/0891 |

* cited by examiner

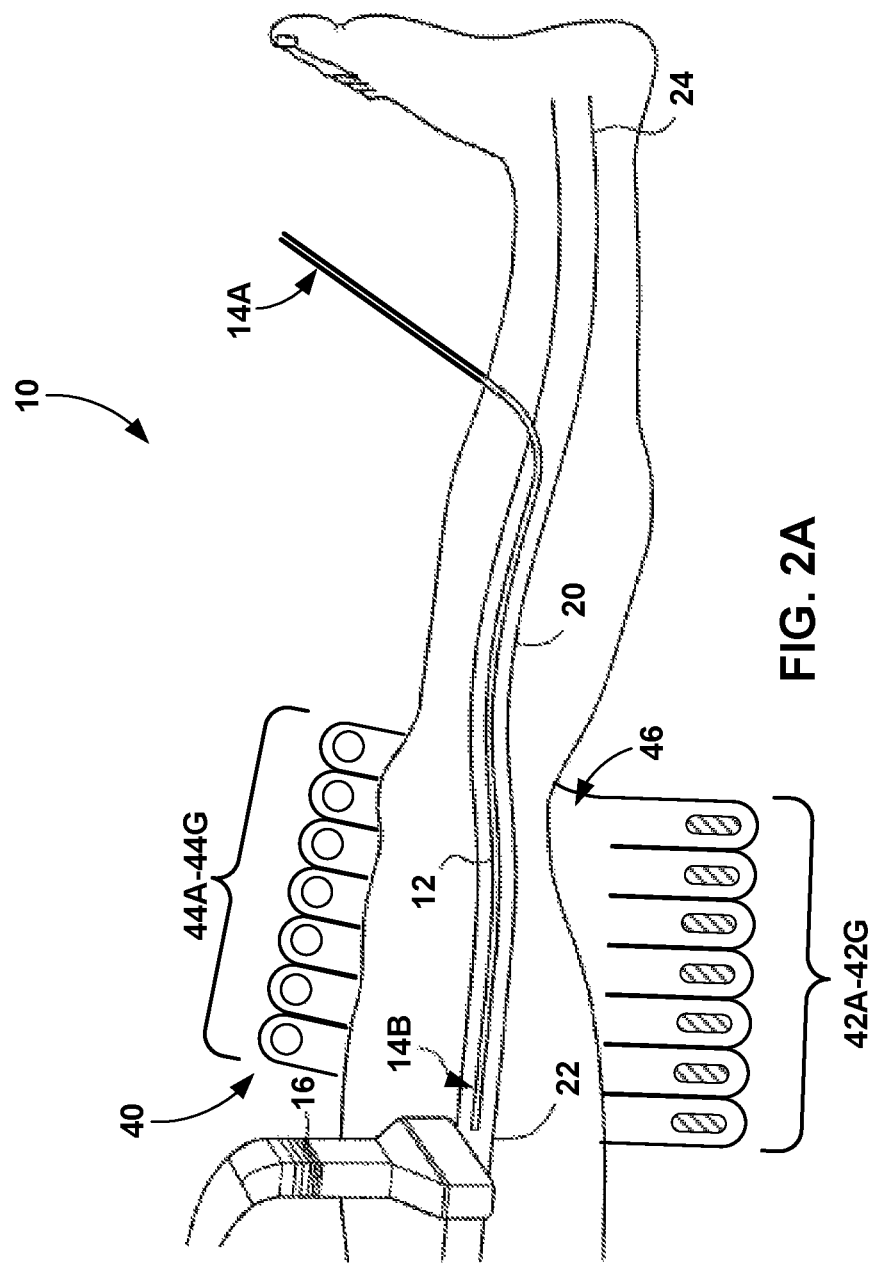

COMPRESSION CUFF

TECHNICAL FIELD

This disclosure relates to medical assemblies and techniques for compressing a hollow anatomical structure within a limb of a patient.

BACKGROUND

Healthy leg veins contain valves that enable blood to move in one direction from the lower limbs towards the heart. These valves open when blood is flowing towards the heart, and close to prevent venous reflux, or the backward flow of blood. When veins weaken and become enlarged, their valves cannot close properly, which can lead to venous reflux and impaired drainage of venous blood from the legs, which may be referred to as venous insufficiency. Venous reflux may occur in the superficial veins. The largest superficial vein is the great saphenous vein (GSV), which runs from the top of the foot to the groin, where it originates at a deep vein.

Many factors may contribute to venous reflux, such as heredity, lack of physical activity, obesity, pregnancy, or jobs that require long periods of standing. Venous reflux can be classified as either asymptomatic or symptomatic, depending on the degree of severity. Symptomatic venous reflux disease is a more advanced stage of the disease and can have a profound impact on a person's quality of life. People with symptomatic venous reflux disease may seek treatment due to a combination of symptoms and signs, which may include leg pain and swelling; painful varicose veins; skin changes such as discoloration or inflammation; and, in the worse cases, open skin ulcers. Some non-invasive methods for treatment of reflux in the greater saphenous vein include radiofrequency (RF) ablation, laser endothermal ablation, and sclerotherapy, including foam sclerotherapy, each of which aims to close the GSV. In a more recent method, a medical adhesive is injected into the GSV, and external compression is applied to the GSV to close the vein by coapting the sides of the vein together.

SUMMARY

In some aspects, this disclosure describes example medical assemblies, devices, systems, and techniques for compressing a portion of a limb of a patient to compress and facilitate closure of a hollow anatomical structure within the limb. For example, a clinician may insert a catheter within the hollow anatomical structure to inject several boluses of adhesive material at different target locations, and a compression cuff described herein applies compression to the limb of the patient before, during, or after injection of the adhesive material. A compression cuff includes a plurality of compression members on each side of the cuff, such that one compression member from each side of the cuff can be wrapped around the limb and attached to each other to create a loop configuration that compresses the limb, and thus a hollow anatomical structure such as a vein, at that location. Other compression members on each side of the cuff and located along the length of the cuff can similarly be wrapped around the limb at respective locations and attached to each other in order to compress the limb, e.g., superficial to each target location that received a bolus of adhesive material. In this manner, compression provided by the loops of the cuff can facilitate coapting the walls of the hollow anatomical structure during setting and/or curing of the adhesive material to close the hollow anatomical structure. This is beneficial to enable the physical to quickly move to the next treatment section without having to manually compress and hold the hollow anatomical structure closed while waiting for the adhesive to cure. In one example, the hollow anatomical structure may be a greater saphenous vein and the limb may be a leg of the patient.

In some examples, each compression member located along one side of the cuff includes a rib on a surface of the compression member that faces the skin when the compression member is in the loop configuration. Each rib may protrude from the surface of the compression member in order to contact and compress the limb. The rib may thus concentrate and direct pressure to the hollow anatomical structure beneath the skin and promote coapting the walls of the hollow anatomical structure with the injected adhesive material.

In one example, a medical assembly configured to compress a portion of a limb of a patient includes a central body, a plurality of medial compression members extending from the central body in a first direction, each medial compression member of the plurality of medial compression members comprising a first attachment element, a rib disposed on at least one of the plurality of medial compression members, and a plurality of lateral compression members extending from the central body in a second direction different than the first direction, each lateral compression member of the plurality of lateral compression members comprising a second attachment element, wherein each first attachment mechanism is configured to attach to the respective second attachment element to create a respective loop configuration with a respective medial compression member and lateral compression member pair to compress the portion of the limb of the patient, wherein the rib is disposed on the at least one medial compression member such that the rib is directed in a radially inward facing direction in the loop configuration, and wherein the rib structure is configured to apply pressure against skin of the patient to compress a vein within the limb.

In another example, a medical system includes a compression cuff configured to compress a portion of a limb of the patient, the compression cuff comprising, a central body, a plurality of medial compression members extending from the central body in a first direction, each medial compression member of the plurality of medial compression members comprising a first attachment element, and a plurality of lateral compression members extending from the central body in a second direction different than the first direction, each lateral compression member of the plurality of lateral compression members comprising a second attachment element, wherein each first attachment mechanism is configured to attach to the respective second attachment element to create a respective loop configuration with a respective medial compression member and lateral compression member pair to compress a portion of the limb of the patient. The medical system also includes a catheter configured to deliver an adhesive material to a hollow anatomical structure within the limb, the catheter comprising a plurality of external markings, each external marking of the plurality of external markings being spaced from an adjacent external marking by a marking spacing that corresponds to a spacing between adjacent medial compression members of the plurality of medial compression members.

In another example, a method for treating a hollow anatomical structure within a patient includes delivering, from a catheter inserted in the hollow anatomical structure, a first bolus of adhesive material to a first target location within the hollow anatomical structure, wrapping a first set of compression members of a compression cuff around the limb to create a first loop configuration around and compressing a first portion of the limb that corresponds to the first target location, wherein the first set of compression members comprises one medial compression member of a plurality of medial compression members extending from a central body in a first direction and one lateral compression member of a plurality of lateral compression members extending from the central body in a second direction different than the first direction, each medial compression member of the plurality of medial compression members comprises a first attachment element and a rib disposed on the respective medial compression member, wherein wrapping the first set of compression members comprises positioning each rib of the respective medial compression member over the hollow anatomical structure to compress a portion of the hollow anatomical structure, and each lateral compression member of the plurality of lateral compression members comprises a second attachment element, each first attachment mechanism being configured to attach to a respective second attachment element to create a respective loop configuration with a respective medial compression member and lateral compression member pair. The method also includes withdrawing the catheter a distance from the first target location to a second target location, delivering, from the catheter inserted into the hollow anatomical structure, a second bolus of adhesive material to the second target location within the hollow anatomical structure, and wrapping a second set of compression members of the compression cuff around the limb to create a second loop configuration around and compressing a second portion of the limb that corresponds to the second target location.

The details of one or more examples are set forth in the accompanying drawings and the description below. Other features, objects, and advantages of examples according to this disclosure will be apparent from the description and drawings, and from the claims.

BRIEF DESCRIPTION OF THE DRAWINGS

FIGS. 2A, 2B, 2C, 2D, and 2E are schematic views of an example procedure for delivering a vein-occluding substance to a patient and compressing portions of a leg with the example compression cuff of FIGS. 1A-1C.

DETAILED DESCRIPTION

Figure 1A:
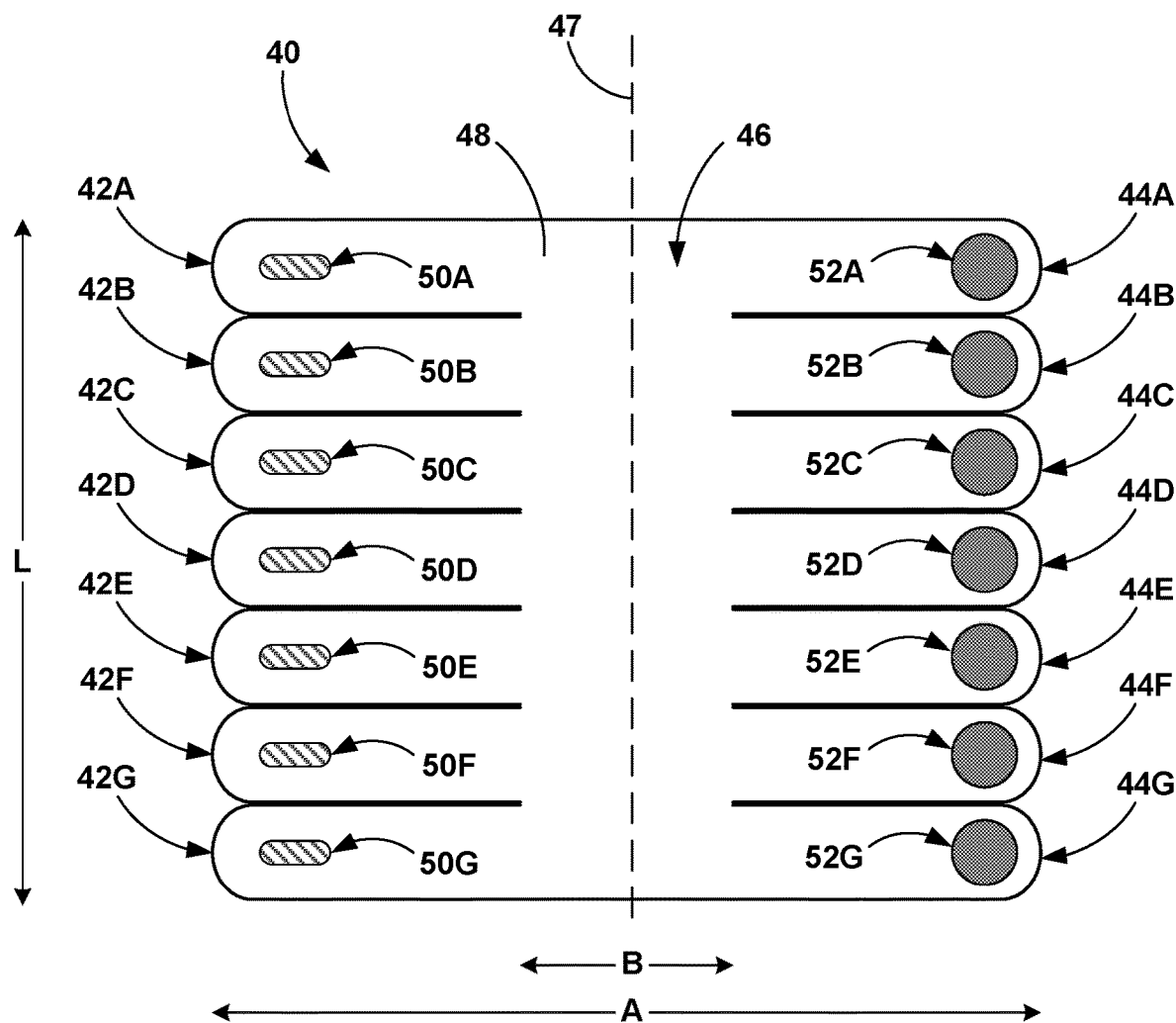
FIG. 1A is a bottom view of an example compression cuff.

This disclosure describes medical assemblies, devices, systems, and techniques for compressing a portion of a limb of a patient to facilitate closure of a hollow anatomical structure (e.g., a vein or an artery) within the limb. Venous reflux or venous insufficiency is a condition in which valves of a vein no longer close properly and blood is able to flow backward within the vein (e.g., a greater saphenous vein or perforator vein). A treatment for venous reflux may include closure or removal of the vein or veins subject to the venous reflux. One example treatment includes delivering a medical adhesive material to the vein such that the medical adhesive coapts the walls of a portion of the vein. Once the medical adhesive cures, the adhered and closed walls of the vein prevent blood from passing through the vein. After the vein is closed, blood can reroute to other veins without compromising systemic blood flow.

An example method for delivering the medical adhesive to the vein may include use of an injector gun (or other device), a syringe, and a catheter. The medical adhesive may be stored in a container (e.g., a vial). A clinician may load the syringe with some or all of the medical adhesive contained within the vial. The clinician can then attach the catheter to the syringe, prime the catheter with the medical adhesive, insert the distal end of the catheter into the target vein, and attach the syringe to an injector gun. When the distal end of the catheter is at the target location within the vein, the clinician can actuate the injector gun which depresses the plunger of the syringe and delivers a bolus of the medical adhesive out of the distal end of the catheter. The clinician may withdraw the catheter proximally (i.e., towards the insertion point in the skin) a short distance one or more times and deliver additional respective boluses of the medical adhesive to other locations within the vein in order to achieve a complete closure of the vein.

These multiple boluses of adhesive that are delivered to respective target locations within the vein must be compressed for a duration of time in order to coapt the vein walls while each bolus of adhesive sets or cures for permanent closure of that portion of the vein. Therefore, in some existing techniques, before the clinician can inject another bolus of adhesive, the clinician must manually compress the skin at a location above where the bolus of adhesive was just delivered in order to at least partially collapse the vein against the adhesive delivered within the vein. The clinician may use a finger or a surface of an ultrasound probe to provide this pressure. The duration of time for which the clinician must hold pressure for each bolus may depend on the composition of the adhesive delivered. The duration of time may be greater than thirty seconds, greater than sixty seconds, or greater than several minutes to ensure that the adhesive has cured and the vein has been closed. For procedures in which several boluses need to be delivered (e.g., four, five, six, or more), the clinician may spend much of the procedure merely holding pressure on the skin to facilitate closure of the vein, which increases the amount of time the clinician needs to complete the procedure. In addition, in some examples, the clinician may need to manually collapse the vein with a finger or ultrasound to create an occlusion in the vein prior to injecting the bolus of adhesive to contain the bolus of adhesive to the target location within the vein.

Systems, devices, assemblies, and techniques described herein may reduce the complexity of medical adhesive delivery and reduce the time required by a clinician to complete a procedure of closing a hollow anatomical structure, such as a vein of a patient. This reduction of complexity and required time for the procedure may improve patient outcomes, reduce procedure cost, and increase clinician efficiency in treating patients. For example, instead of the clinician needing to manually apply pressure to a vein (e.g., a greater saphenous vein in a leg of a patient), a compression cuff having multiple sets of mated pairs of compression members may provide compression at respective locations along the vein as the clinician injects adhesive to different locations within the vein. The clinician may couple a mating pair of compression members to create a loop configuration around the limb (e.g., the leg) that compresses the limb, and thus the hollow anatomical structure, at that location to provide an initial occlusion against which adhesive can be injected and/or to provide pressure that coapts the walls of the vein with the adhesive already delivered. For example, this initial occlusion created by the first set of compression members may prevent migration of the first bolus of adhesive within the hollow anatomical structure.

In this manner, the assemblies and devices described herein, such as a compression cuff, may free a clinician to continually move to the next target location of the vein in the procedure without needing to wait for the adhesive to set or cure (e.g., polymerizes) during application of manual compression. In addition, a set of compression members from a compression cuff are attached to each other to compress a portion of the limb and collapse the vein to form an occlusion, which may free a hand of the clinician to aid in injecting the next bolus of adhesive. Sequential compression along the leg using the next mated pair of compression members may enable, or cause, displacement of the blood from the vein, for example, that may facilitate better closure of the vein with the injected adhesive. Since the clinician may iteratively attach mated pairs of compression members to create respective compressive loops with the compression cuff, the clinician may also continue to use an ultrasound probe to image areas of the limb not yet treated while the previously injected adhesive sets or cures.

In one example, a compression cuff includes a longitudinal axis that runs the length of the compression cuff, and will generally align proximally to distally along a limb of a patient. The compression cuff includes a plurality of compression members on each side of the compression cuff such that one compression member from each side of the cuff can be wrapped around the limb of the patient and attached to each other to create a loop configuration that compresses the limb at that location. Other compression members on each side of the cuff and located along the length (i.e., longitudinal axis) of the cuff can similarly be wrapped around the limb at respective locations and attached to each other in order to compress the limb (either to create an occlusion by collapsing the vein or coapting the walls of the vein with the bolus of adhesive that was delivered). Each mated pair of compression members (e.g., when oriented on a limb of a patient, one compression member extending to a medial side of the cuff and a corresponding compression member extending to the lateral side of the cuff) may be attached to form an individual "band" that can encircle the limb. In this manner, compression provided by the loops of the cuff can facilitate setting and/or curing of the adhesive material to close the hollow anatomical structure. In one example, the hollow anatomical structure may be a greater saphenous vein and the limb may be a leg of the patient. In some examples, medial compression members are described as including one or more structures (such as a rib) different than the lateral compression members on the other side of the cuff. However, lateral compression members may include the respective ribs instead of the medial compression members in other examples.

In some examples, each compression member located along one side of the compression cuff includes a rib or other structure on a surface of the compression member that faces the skin when the compression member is in the loop configuration. The rib structure is a rigid or semi-rigid structure that is configured to resist compressive deformation, e.g., when the compression member is wrapped around a limb of a patient. Each rib may protrude from the surface of the compression member in order to contact and compress the skin of the limb. Each rib thus concentrates and directs pressure from the compression member to the hollow anatomical structure beneath the skin to enable coaptation of the walls of the hollow anatomical structure with the injected adhesive material, or to enable the creation of an obstruction against which the adhesive may be injected. The rib may also enable delivery of pressure to the specific location on the limb above the target location of the hollow anatomical structure without requiring constriction of the entire circumference of the limb, or at least lessening the constrictive force otherwise required to coapt the hollow anatomical structure. Therefore, the rib may help provide sufficient pressure against the skin while reducing compressive pressure at other areas of the limb. In other words, without a rib, the entire circumference of the leg may be constricted to achieve closure of the vein which may reduce blood flow to the entire leg caudal to the constriction. In some examples, each rib may be movable along a length of each compression member. For example, the position of the rib may be adjusted along the compression member closer to or further away from the longitudinal axis of the compression cuff. Such adjustment of the rib enables a physician to best position the rib directly over the hallow anatomical structure, such as the greater saphenous vein, without having to, for example, twist the compression cuff.

Compression cuffs described herein may also be used with other devices that may facilitate delivery of the adhesive to target locations within the patient. For example, a catheter that delivers the adhesive may include external markings that have a marking spacing (e.g., a distance between adjacent markings) corresponding to the spacing of the compression members (specifically the ribs) along the length of the compression cuffs. When the clinician proximally withdraws the catheter such that a distal portion of the catheter is at a new target location within the hollow anatomical structure, the clinician can proximally withdraw the catheter until the next external marking is exposed from a proximal end of an introducer within which the catheter is inserted. Since this exposed marking corresponds to the location of the next compression member on the cuff, the external marking enables the clinician to determine the location at which the next bolus should be delivered to correspond to another set of compression members of the cuff that can compress the walls of the hollow anatomical structure with the delivered bolus of adhesive. The external markings on the catheter may thus reduce or eliminate the need for the clinician to continually measure or use ultrasound imaging between consecutive deliveries of adhesive.

Although the devices and systems described herein are primarily described with reference to delivering a medical adhesive to a vein of a patient and compressing the vein for purposes of treating venous reflux, these systems may be directed to treatment of other conditions or delivery of medical fluid to other locations within a patient. For example, the systems described herein may be configured to deliver wound closure adhesives to an injured hollow anatomical structure (e.g., a blood vessel in the arm) or other tissue and a compression cuff configured to compress tissues at those locations. Although human structures are described herein, other animal species may be treated using the medical assemblies, devices, and techniques described herein.

FIG. 1A is a bottom view of an example compression cuff 40 illustrating the surface of the compression cuff 40 configured to face the limb. As shown in the example of FIG. 1A, the compression cuff 40 includes a plurality of the medial compression members 42 extending from the central body 46 in a first direction. Each of the medial compression members 42 include a respective rib structure 50A, 50B, 50C, 50D, 50E, 50F, and 50G (collectively "the rib structures 50") that is carried on the surface 48 that is facing radially inward in the loop configuration of the cuff 40. The compression cuff 40 also include a plurality of lateral compression members 44 extending from the central body 46 in a second direction that is different from the first direction. Although the first and second directions are shown as being opposite from each other (e.g., 180° apart), the first direction may be oblique from the second direction in other examples. Each of the lateral compression members 44 include a respective attachment element 52A, 52B, 52C, 52D, 52E, 52F, and 52G (collectively "the attachment elements 52") that is carried on the surface of the respective lateral compression member 44 that is facing radially inward in the loop configuration.

The compression members 42 and 44 are configured to be flexible in a circumferential direction (i.e., the Z direction or the direction out of plane of the compression cuff 40) such that each of the compression members 42 and 44 may be bent out of the plane of the compression cuff 40 to create respective loops. In some examples, the compression members 42 and 44 may be relatively unstretchable. In other examples, the compression members 42 and 44 may be stretchable or elastic in order to provide the compression against a limb. The compression members 42 and 44 may be constructed of at least one of a woven textile, a non-woven textile, or one or more polymers. Similarly, the central body 46 may be constructed of at least one of a woven textile, a non-woven textile, or one or more polymers in some examples. However, the central body 46 may be constructed to be less flexible than, or constructed of materials that are less flexible than, the materials used for the compression members 42 and 44.

Generally, the compression cuff 40 may include two or more of the medial compression members 42 and the lateral compression members 44. In some examples, the compression cuff 40 includes at least five of the medial compression members 42 and at least five of the lateral compression members 44. As shown in the example of FIG. 1A, the compression cuff 40 includes seven medial compression members 42 and seven lateral compression members 44. In some examples, the compression cuff 40 may include a certain number of compression members 42 and 44 that varies based on the particular hollow anatomical structure to be treated and/or the type of adhesive to be used during the procedure. A greater saphenous vein, for example, may require six to eight boluses of adhesive over a relatively long treatment length of the vein. Therefore, compression cuff 40 may include eight sets of compression members 42 and 44, for example. Generally, the compression cuff 40 includes an equal number of the medial compression members 42 and the lateral compression members 44. However, in other examples, an unequal number of compression members 42 and 44 may be used in some examples (e.g., to accommodate bends in anatomy, avoid sensitive tissue, to treat tortuous hollow anatomical structures, or for any other reason).

The compression cuff 40 and the compression members 42 and 44 may have any suitable width which is the direction running parallel with the longitudinal direction and the length L of the compression cuff 40. In some examples, each of the compression members 42 and 44 may have a width from approximately 0.5 cm to approximately 5.0 cm. In other examples, each of the compression members 42 and 44 may have a width from approximately 1.0 cm to approximately 3.0 cm. The length of each of the compression members 42 and 44, as measured from the central body 46 and in the same direction as width B, may be from approximately 5.0 cm to approximately 50 cm. Central body 46 is described, in one example, as ending along a line that intersects the end of the split between adjacent compression members 42 and 44. In other examples, the length of each of the compression members 42 and 44 may be from approximately 10 cm to approximately 30 cm. The central body 46 may have a width B between approximately 10 cm to approximately 40 cm. The total width A that includes the length of the compression members 42 and 44 and the central body 46 may be between approximately 30 cm to approximately 140 cm. However, width B, width A, and the lengths of the compression members 42 and 44 may be larger or smaller than the example ranges described above.

Although all of the compression members 42 and 44 preferably have the same length and width in some examples, the length and/or width of the compression members 42 and 44 may be different within the same compression cuff 40 in other examples. For example, the medial compression members 42 may be longer than the lateral compression members 44. In some examples, one medial compression member 42 may have a different length and/or width than another medial compression member 42, and/or one lateral compression member 44 may have a different length and/or width than another lateral compression member 44. For example, the length of the compression members 42A and 44A may be longer than the length of the compression members 42G and 44G to accommodate a typically larger leg circumference in the middle of the leg as compared to the leg circumference closer to the knee of the patient. In this manner, the compression cuff 40 would have to be constructed with dimensions configured for different types of limbs or other anatomical regions, different sizes of patients, or different types of procedures. However, it is preferred that the compression cuff 40 is symmetrical along the longitudinal axis 47. Configuring the compression cuff 40 symmetrically enables the compression cuff 40 to be used in either orientation on any limb (i.e., a clinician does not have to orient the compression cuff with any particular end superior on the limb), thereby saving procedure time. Further, configuring the compression cuff 40 to be symmetrical enables a clinician to orient the medial compression members 42 towards the medial side of the limb whether the procedure is on the right limb or the left limb. Further, clinician could orient the medial compression members 42 towards the lateral side of the limb if the clinician is more comfortable wrapping the medial compression member 42 and lateral compression member 44 in that orientation.

The compression cuff 40 may have any suitable length L. For example, the length L of the compression cuff 40 may be selected from approximately 10 cm to approximately 60 cm. The length L may be selected based on the number of desired compression members 42 and 44 or other factors, such as the type of limb for which the compression cuff 40 is intended to be used, the size of the patient, and the like. In some examples, the compression cuff 40 may have a length L selected to be large enough to compress all locations treated with adhesive. In some examples of treating the vein 20, the total treatment site may have a length from approximately 2 cm to approximately 50 cm, or from approximately 5 cm to approximately 40 cm in other examples. Therefore, length L of the compression cuff 40 may be selected from approximately 10 cm to approximately 60 cm.

As shown in FIG. 1A, in some examples, adjacent medial compression members 42 and adjacent latera compression members 44 may touch or almost touch in the flat configuration (as shown in FIG. 1A) or in the loop configuration around the limb. For example, adjacent medial compression members 42 may be separated from each other by a distance less than approximately 0.5 cm, and adjacent lateral compression members 44 may be separated from each other by a distance less than approximately 0.5 cm. In some examples, portions of some or all adjacent medial compression members 42 and lateral compression members 44 may even partially overlap in order to provide compression at the desired locations along the limb. Similar to the example of FIG. 4, the compression members 42 and 44 may be separated by larger distances (X) in other examples.

In some examples, the medial compression members 42, the lateral compression members 44, and the central body 46 may together form a unitary structure. For example, the medial compression members 42, the lateral compression members 44 and the central body 46 may be cut from a single piece of material or formed into a single piece of material. In other examples, the central body 46 may be formed from a plurality of central sections coupled together in series. Each of the central sections may be attached to or formed with a single respective one of the medial compression members 42 and the lateral compression members 44. In this manner, each central section and its respective compression member 42 and 44 may form a "band" that can be removably coupled with other "bands" to create a complete compression cuff similar to the compression cuff 40. In some examples, each central section may attach to another central section via a hook and loop closure, snaps, zipper, buckle, or any other type of attachment mechanism. In other examples, each central section may include two or more medial compression members 42 and two or more lateral compression members 44. A compression cuff formed by several attached "bands" may enable a clinician to customize the length L of the compression cuff 40 for the specific patient and/or treatment length of the hollow anatomical structure. Further, attaching the several "bands" enables a clinician to save time during the procedure because the clinician is not manipulating several separate bands, but instead placing a single device under the patient before beginning the procedure.

The rib structures 50 may each be attached to a surface of a respective medial compression member 42 (or lateral compression member 44 in other examples). When in the loop configuration, the surface carrying the rib structures 50 will be a radially inward facing surface 48 such that the each of the rib structures 50 can directly contact (e.g., touch skin) the limb and apply pressure to compress the vein within the limb. The rib structures 50 are shown in FIG. 1A has having an oval cross-sectional shape, similar to an ultrasound transducer, but other cross-sectional shapes such as rectangles, squares, or non-linear shapes may be used for the rib structures 50. The rib structures 50 may be formed to have the longer dimension running parallel to the length of the medial compression members 42 in order to provide pressure to the hollow anatomical structure even if the rib structure 50 is not perfectly centered over the hollow anatomical structure. In some examples, the rib structures 50 may have a contact shape similar to the contact shape of an ultrasound transducer that may be placed against the skin of the patient during imaging of the hollow anatomical structure to be treated. In this manner, the rib structures 50 may have a flat surface that contacts the skin of the patient. In other examples, the rib structures 50 may have a curved or semi-circular surface that contacts the skin of the patient, which may correspond to the curve of the loop configuration.

In some examples, each of the rib structures 50 may have a length from approximately 1.0 cm to approximately 10 cm, and more preferably 2 cm to 5 cm. The width of each of the rib structures 50 may be less than the width of the respective medial compression member 42, such as a width from approximately 0.3 cm to approximately 2 cm. However, the connection mechanism (for example a slot through which the medial compression member 42 passes) may be slightly wider than the width of the medial compression member. In some examples, each of the rib structures 50 may have a height (e.g., the distance protruding from the respective compression member 42) selected from approximately 0.5 cm to approximately 3 cm, but other heights may be used in other examples. Each of the rib structures may have a cross-section shape that is a quadrilateral, square, rectangle, trapezoid, triangle or any other shape. In some examples, the cross-sectional shape may have rounded corners to reduce potential skin irritation. In some examples, the rib structures 50 may have different dimensions and/or cross-sectional shapes on different ones of the compression members 42 in order to target different areas of tissue that need to be compressed or to provide different types of pressure to the hollow anatomical structure.

The rib structures 50 may be constructed of any rigid or semi-rigid material such as at least one of a polymer, composite material, rubber, or metal or metal alloy. In other examples, the rib structure 50 may be a viscous gel or malleable polymer encased in a pliable membrane. In some examples, the rib structures 50 may be permanently attached to the respective medial compression member 42 using an adhesive, stitching, clamp, or any other type of permanent fastener. In other examples, the rib structures 50 may be movably attached to the medial compression member 42 to enable a clinician to adjust the location of the rib structure 50 on the medial compression member 42. In this manner, the clinician may move each rib structure of the rib structures 50 in a lateral direction in order to provide pressure to the limb directly above the location of the hollow anatomical structure to be treated. In some examples, the rib structure 50 may be attached with a hook and loop fastener. In other example, the ribs structure may be slidably attached to the medial compression member 42 through a slot within the rib structure 50 through which the medial compression member slides. In yet another example, the rib structure 50 may be inserted into an elongate pocket formed within the respective medial compression member 42, wherein the elongate pocket is longer then the rib structure to enable the rib structure to be placed at different locations within the pocket. Although rib structures 50 may be formed separately from the compression member 42 and then attached, the rib structures 50 may be formed as a part of the compression members 42 in other examples.

Figure 1B:
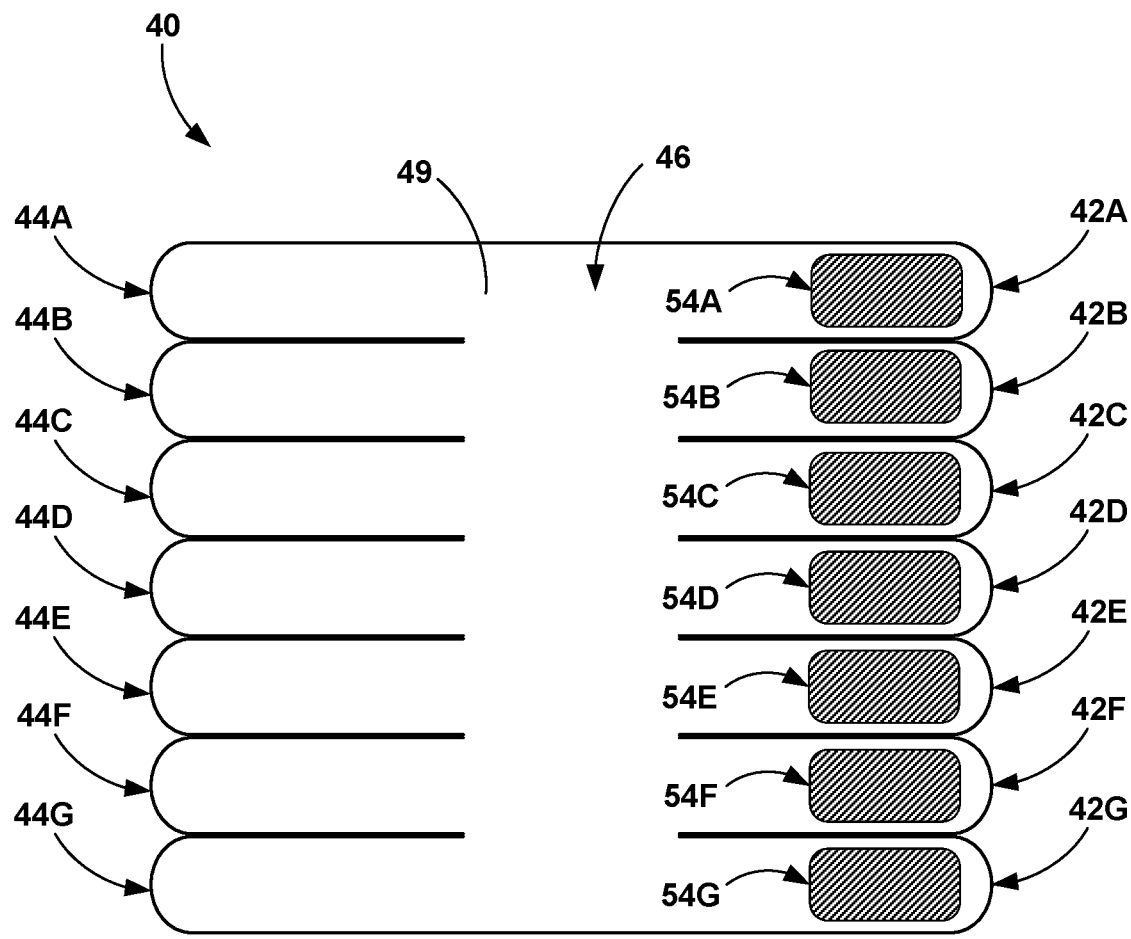
FIG. 1B is a top view of the example compression cuff in FIG. 1A.

FIG. 1B is a top view of the example compression cuff 40 in FIG. 1A, and illustrates an opposite side of the compression cuff 40 from that shown in FIG. 1A. As shown in the example of FIG. 1B, each of the medial compression members 42 include a respective attachment element 54A, 54B, 54C, 54D, 54E, 54F, and 54G (collectively "the attachment elements 54") that is carried on a surface 49 of the medial compression members 42 that faces away from the limb of the patient when the cuff 40 is in the loop configuration. The attachment elements 54 are configured to mate with the attachment elements 52 of the lateral compression members 44 shown in FIG. 1A. In some examples, the attachment elements 54 may be larger (e.g., longer) than attachment elements 52 to enable attachment with the attachment elements 52 at different locations and facilitate the creation of loop configurations with different circumferential lengths with the respective compression members 42 and 44.

Figure 1C:
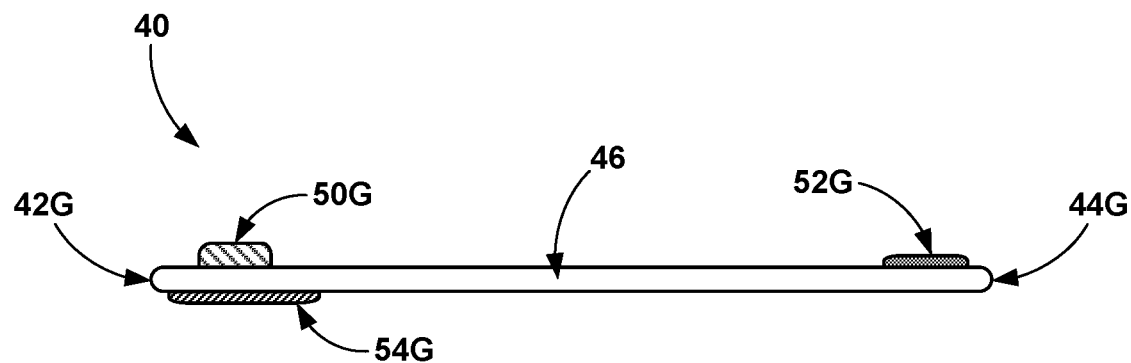
FIG. 1C is a side view of the example compression cuff in FIG. 1A.

FIG. 1C is a side view of the example compression cuff 40 in FIG. 1A. As shown in the example of FIG. 1C, the longitudinal end of the compression cuff 40 is shown to include the compression members 42G and 44G, the central body 46, the attachment elements 52G and 54G, and the rib structure 50G. FIG. 1C illustrates the flat configuration of the compression cuff 40. The clinician wraps both of the medial compression member 42G and the lateral compression member 44G up and into a loop configuration such that the end of the lateral compression member 44G wraps over the end of the medial compression member 42 and the attachment element 52G engages with the attachment element 54G. The attachment elements 52G and 54G may be configured to support multiple locations for attachment along the length of the medial compression member 42, such as with a hook and loop closure system, a buckle, or any other type of attachment elements.

The attachment elements 52 and 54 together form an attachment mechanism that secures the medial compression members 42 to the respective lateral compression members 44. In one example, each of the attachment elements 54 include a plurality of loops and each of the attachment elements 52 include a plurality of hooks that are configured to secure to the plurality of loops. This type of attachment mechanism may be referred to as a hook and loop closure system. In other examples, attachment elements 52 and 54 may include one or more snaps, tabs, buttons, clamps, buckles, or any other type of removable attachment element. In any case, the attachment elements 52 and 54, when connected, may be configured to maintain the compression needed to close the hollow anatomical structure to be treated.

Figure 2B:
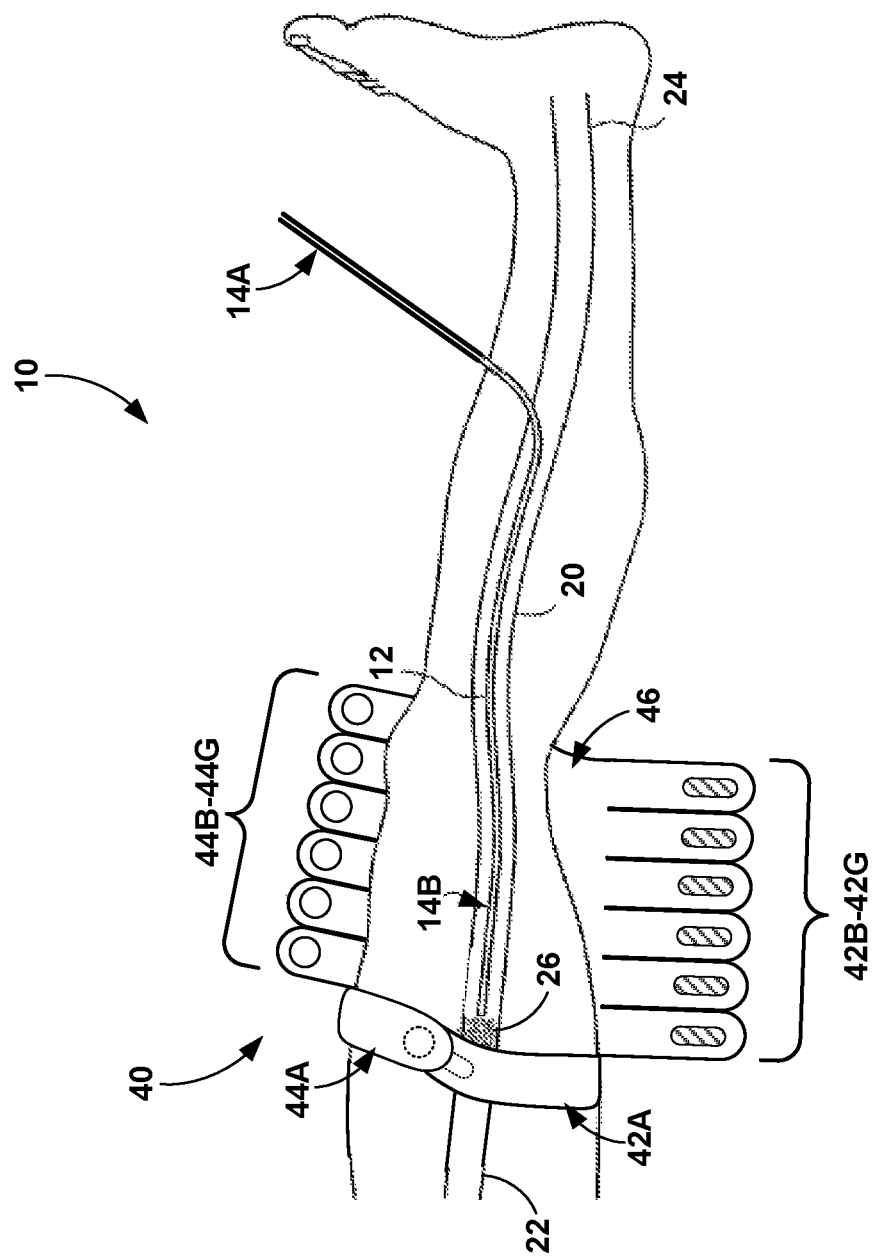

FIGS. 2A, 2B, 2C, 2D, and 2E are schematic views of an example procedure for delivering a vein-occluding substance to a hollowing anatomical structure in a leg of a patient and compressing portions of the leg with the example compression cuff 40 shown in FIGS. 1A-1C. As shown in FIG. 2A, the medical assembly 10 includes the compression cuff 40, which has been placed under a leg of the patient, and a flexible catheter 12, with a proximal end 14A and a distal end 14B. The flexible catheter 12 has been inserted into a vein 20 of the patient. The vein 20 may be a greater saphenous vein in some examples, but the vein 20 may be any superficial, deep, or perforator vein in other examples. The vein 20 may include an inferior portion 24 and a superior portion 22. A dispenser gun, syringe, or other pressurizing device (not shown) may hold a volume of medical adhesive material (e.g., medical adhesive 26 shown in FIGS. 2B-2E) and deliver the medical adhesive through the proximal end 14A of the flexible catheter 12, to the distal end 14B and out of the distal end 14B of the flexible catheter 12. The flexible catheter 12 is configured to be disposed within a hollow anatomical structure (e.g., the vein 20) of a patient. The flexible catheter 12 may be an elongated structure (e.g., a tubular body) defining at least one lumen having a lumen cross-sectional dimension (e.g., a diameter in the case of a cylinder), a proximal opening of the lumen near the proximal 14A of the flexible catheter 12, and a distal opening of the lumen near or at the distal end 14B of the flexible catheter 12.

A clinician may use an imaging tool such as an ultrasound transducer 16 to image the vein 20 and/or to assist in guiding the flexible catheter 12 to the target location(s) that will receive the medical adhesive. The ultrasound transducer 16 may be multifunctional. For example, the ultrasound transducer 16 may include one or more ultrasound sensors used to generate an image that helps a clinician guide the catheter 12 (or another device, such as a guide catheter or a guidewire) through vasculature of a patient, may serve as a compression element to the vein 20 after a bolus of medical adhesive is delivered in the vein 20, and/or identifying areas in the interior of the vein 20 that may need further occlusion or closure. However, as described herein, the compression cuff 40 is configured to provide compression to target locations within vein 20 instead of or in addition to the manual application of compressive force applied by a clinician via the ultrasound transducer 16 or via another tool or the clinician's hand. In some examples, the ultrasound transducer 16 can be placed into contact with an external surface of a patient's skin prior to placing the flexible catheter 12 or any other devices (e.g., an introducer catheter or guidewire through vessel 20). For example, the clinician may use the ultrasound transducer 16 to map out and mark the target vessel to enable more accurate placement of the compression cuff 40, and more specifically, more accurate placement of the rib structures 50. The ultrasound transducer 16 can assist in generating images to help guide one or more catheters or guide devices to the target site or sites where a vein-occluding substance (e.g., a medical adhesive) will be introduced. In some examples, the ultrasound transducer 16 can include a Doppler flow detection capability, and help to identify areas in the interior of the vein 20 that may need further closure or occlusion and thus, further application of a vein-occluding substance.

In some examples, the flexible catheter 12 may include one or more features that promote visualization of one or more portions of the flexible catheter 12 under ultrasound visualization with the ultrasound transducer 16. For example, the flexible catheter 12 may include one or more echogenic portions at the distal portion of the flexible catheter 12. The echogenic portion may include one or more cavities defined in the wall of the flexible catheter 12. These cavities may be disposed circumferentially, axially, and/or or radially within the wall of the flexible catheter 12. The cavities may include a gas (e.g., air or nitrogen), a solid material (e.g., a metal alloy), or some other material that can be differentiated from other anatomical structures or fluids within the patient. In some examples, the cavities may be formed by the material used to construct the wall of the flexible catheter 12 or the cavities may be defined by a material that captures air within a porous membrane (e.g., expanded polytetrafluorethylene (EPTFE)).

As shown in FIG. 2B, medial compression member 42A and lateral compression member 42B from compression cuff 40 is a mated pair or set of compression members and has been wrapped around the leg of the patient to create a loop configuration that provides a compressive force against the leg and the portion of the vein 20. In particular, medial compression member 42A and lateral compression member 42B creates an initial occlusion in the vein 20 (e.g., forces the walls of the vein 20 to touch so that blood or other fluids cannot flow past that occluded portion of the vein 20. As discussed herein, the compression cuff 40 includes medial compression members 42A, 42B, 42C, 42D, 42E, 42F, and 42G (collectively "the compression members 42") extending in a first direction and lateral compression members 44A, 44B, 44C, 44D, 44E, 44F, and 44G (collectively "the compression members 44") extending in a second direction that is different than the first direction. The medial compression members 42A-G will wrap generally towards the medial direction of the patient, while the lateral compression members 44A-G will wrap generally towards the lateral direction of the patient.

Figure 2C:
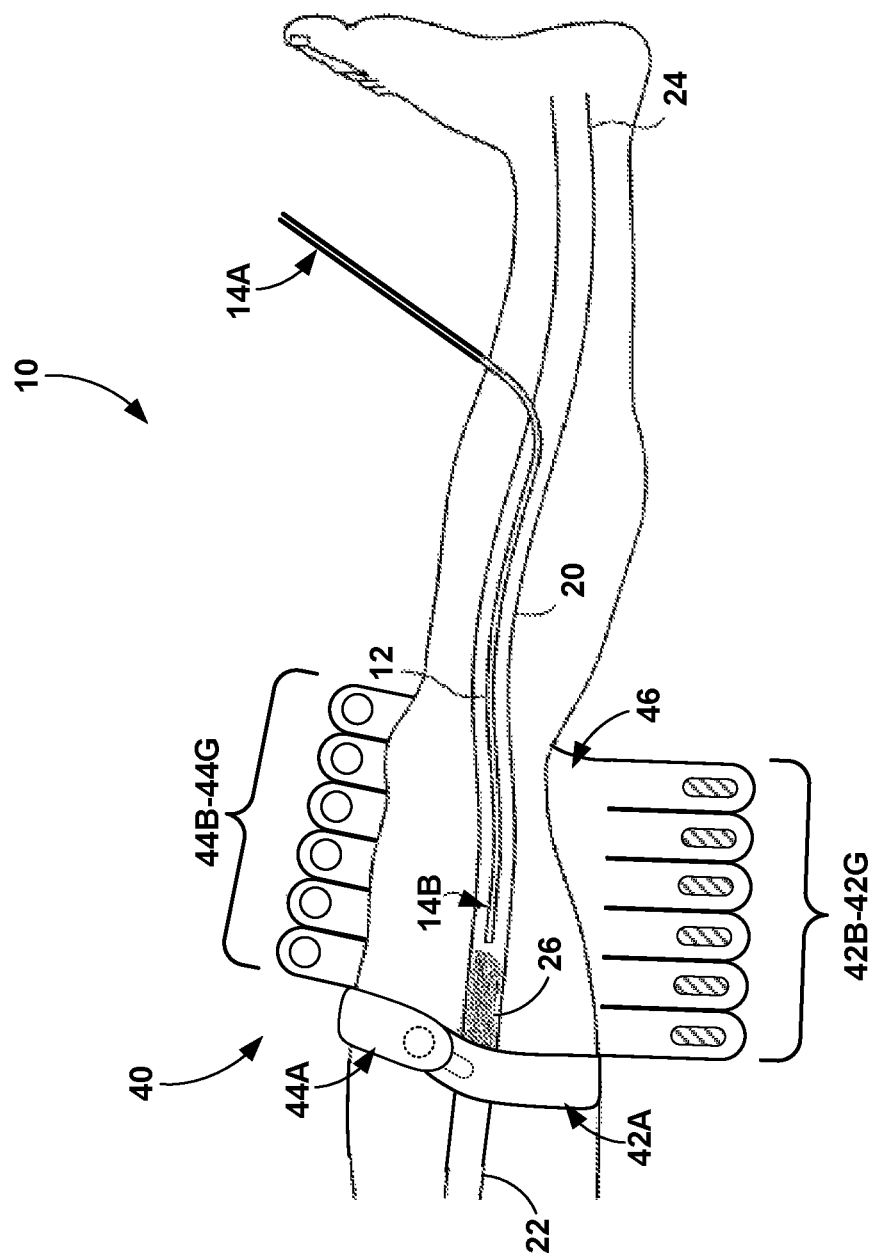

Subsequent to wrapping compression members 42A and 44A around the leg, the clinician can inject the bolus 26 of the medical adhesive out of the distal end 14B of the flexible catheter 12 and against the occlusion. In other examples, the ultrasound transducer 16 can be pressed against the leg to create the initial occlusion in the vein 20 against which the bolus 26 can be delivered. As shown in FIG. 2C, the bolus 26 of the medical adhesive has been fully delivered into the vein 20 and the clinician has proximally withdrawn the flexible catheter 12 from the site at which the bolus 26 was delivered.

Figure 2D:
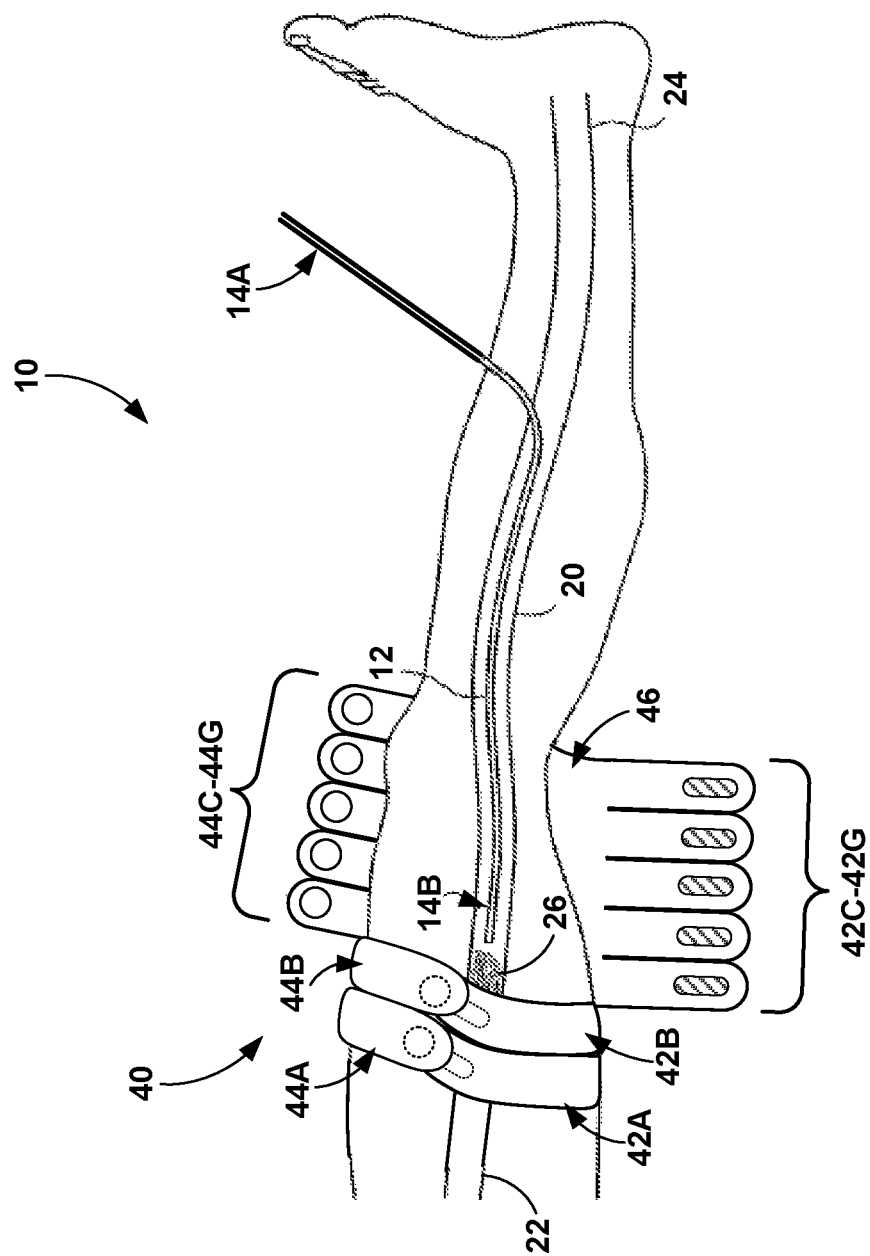

As shown in the example of FIG. 2D, once the flexible catheter 12 is removed from the area containing the bolus 26, the clinician applies pressure to that portion of the vein 20 with the next pair of compression members, such as medial compression member 42B and lateral compression member 44B. Each of the medial compression members 42 and the lateral compression members 44 are independently movable to enable sets of the compression members 42 and 44 to be independently coupled together as needed during a medical procedure. For example, as shown in FIG. 2D, the medial compression members 42B and the lateral compression member 44B are mated pairs and have been wrapped around the leg of the patient to create a loop configuration that provides a compressive force against the leg and the portion of the vein 20 that includes the bolus 26. The compression cuff 40 is configured such that a clinician may adjust the position of the attachment between the compression members 42B and 44B in order to customize the circumference of the loop created by the compression members 42B and 44B and the resulting amount of compression applied to the leg. This compression assists in occlusion as well as collapse of the vein 20 in order to coapt the vessel walls.

After delivering the bolus 26 and coupling the compression members 42B and 44B to compress the portion of the vein including the bolus 26, the clinician may leave the compression cuff 40 in place and proximally withdraw the flexible catheter 12 to move the distal end 14B to a new location within the vein 20 and repeat the process shown in FIGS. 2B-2D in order to deliver another bolus of the medical adhesive to the new location within the vein 20. In some examples, different target locations for delivery of the medical adhesive may be spaced apart from an adjacent target location by approximately 0.5 centimeters (cm) to approximately 7 cm along the length of the vein 20. More preferably, the different target locations, and thus the different bolus 26 of adhesive, are spaced between 1 cm and 3 cm apart. In some examples, the total treatment length of the vein 20 may have a length between approximately 2 cm and approximately 50 cm, or between approximately 5 cm and approximately 40 cm in some examples.

In one example, the catheter 12 may include a plurality of external markings (e.g., external markings 112A-112E shown in FIG. 6), each marking spacing being separated from an adjacent marker by a marking spacing (measured in units of distance) that corresponds to a spacing between adjacent compression members 42 and/or adjacent the compression members 44. As the clinician proximally withdraws the catheter 12 from an introducer sheath, exposure of the next external marking on the catheter 12 indicates that the distal end 14B is at the next target location within the vein 20. Thus, the external markings may provide a visual aid with which a clinician may deliver boluses of the adhesive 26 at target locations within the vein 20. By having the spacing between external markings 112A-112E correspond to the spacing between the compression members 42 and 44, the time required to reposition the catheter 12, deliver a bolus of adhesive 26, and apply pressure to the bolus 26 may be reduced, thereby reducing the total procedure time.

Figure 2E:
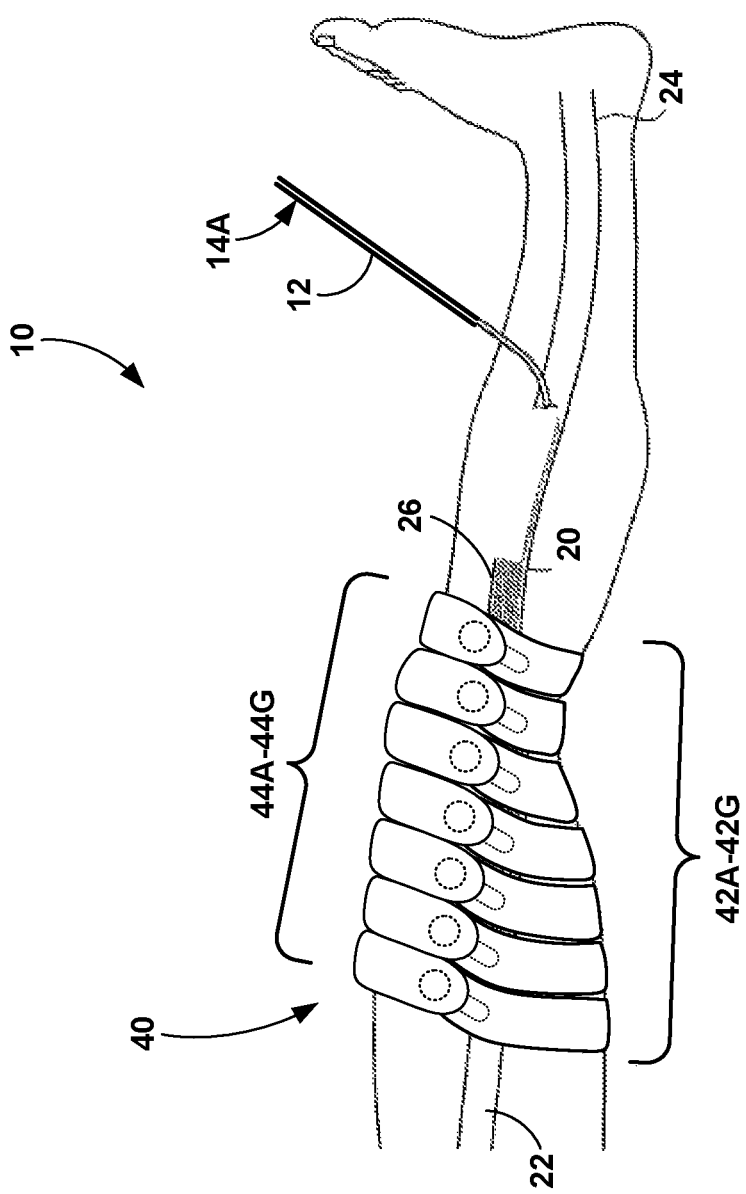

In FIG. 2E, all of the compression members 42 have been coupled to respective mated pair of compression members 44 in order to provide compression for all of the target locations at which the entire bolus 26 has been delivered to the vein 20. In other examples, the clinician may not need to use all of the compression members 42 and 44 when the treatment length of the vein 20 is shorter than the length of the compression cuff 40. The compression cuff 40 may be left in the closed configuration shown in FIG. 2E as long as needed for all of the boluses (e.g., all of the adhesive material) to set or cure (e.g., polymerize). For example, the compression members 42 and 44 may remain coupled to provide compression for a duration of no more than about 5 minutes, 4 minutes, 3 minutes, 2 minutes, 1 minute, 30 seconds, 15 seconds, or less following injection of the last bolus of adhesive. In some examples, the clinician may decouple all of the compression members 42 and 44 at the same time. In other examples, the clinician may decouple the compression members 42 and 44 in reverse order from their coupling in order to maintain a desired duration of compression at each location. For example, the compression members 42A and 44A may be decoupled before compression members 42B and 44B are decoupled.

Figure 3:
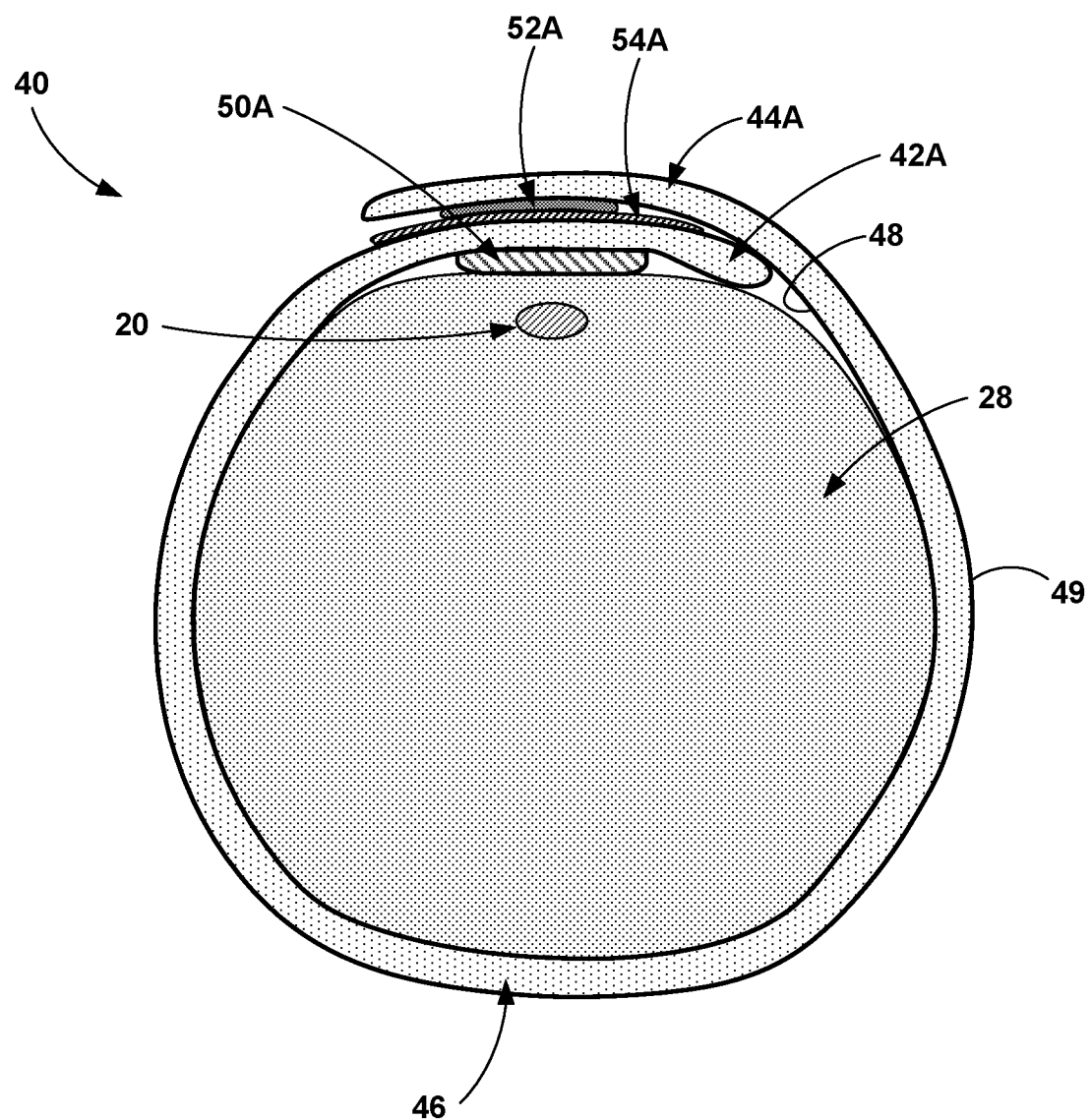
FIG. 3 is a cross-sectional view of a limb compressed by compression members of the example compression cuff of FIGS. 1A-1C.

As described herein, the compression cuff 40 may be an example medical assembly that is configured to compress a portion of the limb of the patient. The example compression cuff 40 shown in FIGS. 1A-3 includes a central body 46 having a longitudinal axis 47, an internal surface 48 and an external surface 49. In use, the internal surface 48 will face the patient's skin and the external surface 49 will face away from the patient's skin. The compression cuff 40 includes a plurality of the medial compression members 42 extending from the central body 46 (shown in FIG. 1A) in a first direction, where each of the medial compression members 42 include a respective attachment element 54. The compression cuff 40 also includes a plurality of the lateral compression members 44 extending from the central body 46 in a second direction different than the first direction, where each of the lateral compression members 44 include a respective attachment element 52. The attachment elements 54 of the medial compression members 42 are configured to attach or couple to respective attachment elements 52 of the lateral compression members 44. When coupled, each pair of one of the medial compression members 42 and one of the lateral compression members 44 creates a respective loop configuration to compress a portion of the limb of the patient, as shown in FIGS. 2E and 3.

The attachment elements 52, 54 may include respective mating elements, such as hooks and loops to create a hook and loop attachment mechanism, buttons and slots, snaps, tabs, temporary adhesive, indents and detents, or any other types of materials or structures configured to create a removable connection. Preferably the attachment elements 52, 54 are hook and loop attachments to give greater flexibility in adjusting the size of the loop, and thus the compressive forces generated. In addition to the attachment elements, in some examples, each of the compression members 42 includes a rib structure (e.g., rib structure 50A of FIG. 3) configured to apply more focused pressure against skin of the patient compared to compression members 42 without a rib structure to more effectively compress a target vein 20 within the limb. For example, each rib structure may be attached to a surface of the respective compression member 42, where the surface is the internal surface 48 when in the loop configuration.

As shown in FIG. 2E, multiple boluses of the medical adhesive have been delivered to the vein 20 in order to coapt the vein 20 with the adhesive and create an occluded portion of the vein 20. The occluded portion may include medical adhesive that has been delivered from the catheter 12 and into the vein 20 and adhered to the walls of the vein 20. In some examples, the occluded portion may include a continuous length of medical adhesive caused by multiple delivered boluses. In other examples, the occluded portion 30 may include multiple separate areas of the vein 20 that have been coapted by the medical adhesive with the aid of the compression cuff 40. After the medical adhesive is delivered, the clinician may remove the flexible catheter 12 from the vein 20 and the patient.

In some examples, the medical adhesive described herein may have a viscosity between approximately 40 centipoise (cP) and 3,000 cP, preferably between 1,000 cP and 2,500 cP. Each bolus of medical adhesive delivered to a single location within the vessel may be in a range of approximately 0.01 cubic centimeters (cc) to 3 cc. In other examples, each bolus may be in a range of approximately 0.05 mL to 0.5 mL, approximately 0.1 mL to 0.2 mL, or approximately 0.01 cc to 1.0 cc of medical adhesive. Each bolus may be spaced approximately 2 cm to 6 cm or approximately 0.5 to 5 cm apart.

Example medical adhesives may include cyanoacrylate (e.g., 2-octyl cyanoacrylate). In some examples, a cyanoacrylate can be an aliphatic 2-cyanoacrylate ester such as an alkyl, cycloalkyl, alkenyl or alkoxyalkyl2-cyanoacrylate ester. The alkyl group may have from 1 to 16 carbon atoms in some embodiments, and can be a C1-C8 alkyl ester or a C1-C4 alkyl ester. Some possible esters include the methyl, ethyl, npropyl, isopropyl, n-butyl, isobutyl, pentyl, hexyl, cyclohexyl, heptyl, octyl, 2-methoxyethyl and 2-ethoxyethyl esters of cyanoacrylic acid. Other medical adhesives that can be used include a biological glue such as a bovine serum albumin-gluteraldehyde combination (e.g., BIOGLUE, Cryolife, Atlanta, Ga.), PVA, Biogard, collagen, fibrinogen, fibronectin, vitronectin, laminin, thrombin, gelatin, mixtures thereof, or other biocompatible adhesives. A preferred medical adhesive is a n-butyl cyanoacrylate, such as VenaSeal™ adhesive, sold by Medtronic, Inc.

In some examples, the adhesive can also include a therapeutic agent such as an anti-inflammatory agent, an anti-infective agent, an anesthetic, a pro-inflammatory agent, a cell proliferative agent, or combinations thereof. In some examples, the medical adhesives, such as the cyanoacrylate adhesives, can have select properties. In some examples, the medical adhesives can have a setting time of between about 5 to 60 seconds. However, longer set times are possible without extending the procedure time because the compression cuff 40 enables the clinician to continue the procedure without waiting for the adhesive to polymerize or set.

As discussed herein, the compression cuff 40 may be used in a procedure to treat a hollow anatomical structure of the patient. For example, the technique may include injecting, from the catheter 12 inserted into the hollow anatomical structure of the patient, a first bolus (e.g., the bolus 26) of adhesive material to a first target location and then mechanically connecting one of the medial compression members 42 (e.g., the medial compression member 42A) with another one of the lateral compression members 44 (e.g., the lateral compression member 44A) of the compression cuff 40 to create a first loop configuration around and compressing a first portion of the limb that corresponds to the first target location. The technique may then include withdrawing the catheter 12 a distance from the first target location to a second target location, injecting, from the catheter 12 inserted into the hollow anatomical structure of the patient, a second bolus of the adhesive material to the second target location, and then mechanically connecting another one of the medial compression members 42 (e.g., the medial compression member 42B) and another one of the lateral compression members 44 (e.g., the lateral compression member 44B) of the compression cuff 40 to create a second loop configuration around and compressing a second portion of the limb that corresponds to the second target location. This technique may continue iteratively until the clinician has treated all of the desired target locations of the vein 20.

In some examples, some of the compression members 42 and 44 may be used to create an occlusion in the vein 20 prior to injecting the bolus 26. For example, one of the medial compression members 42 may be coupled to one of the lateral compression members 44 to form the loop configuration and create the occlusion in the vein 20. Then, the clinician may inject the bolus 26 proximal to and adjacent to the occlusion and wrap the next set of the compression members 42 and 44 into the loop configuration to compress the delivered bolus. In some examples, respective sets of the compression members 42 and 44 may be used to form occlusions distal from each bolus injected into the vein 20. In this example use of compression cuff 40, first medial compression member 42A will be coupled to lateral compression member 44A to create an occlusion, and then a first bolus of adhesive is injected against the created occlusion. Then, medial compression member 42B will be coupled to lateral compression member 44B to compress and coapt the vein into the first bolus of adhesive. Next, medial compression member 42C will be coupled to lateral compression member 44C to create another occlusion, and then a second bolus of adhesive is injected against that created occlusion. Then medial compression member 42D will be coupled to lateral compression member 44D to compress and coapt the vein into the second bolus of adhesive. Next, medial compression member 42E will be coupled to lateral compression member 44E to create another occlusion, and then a third bolus of adhesive is injected against that created occlusion. Then, medial compression member 42F will be coupled to lateral compression member 44F to compress and coapt the vein into the third bolus of adhesive. In some examples, medial compression member 42G will be coupled to lateral compression member 44G to create another occlusion against which a fourth bolus is injected or to coapt the vein into another bolus of adhesive. In some examples, members 42G and 44G may not be needed for the procedure, or more lateral and medial compression members may be provided to facilitate additional treatments along the limb. In examples in which the medial compression members include a respective rib, wrapping the respective compression member around the leg would include positioning the respective rib over the target vein in order for the rib to apply compressive force against the target vein. In some examples, fewer than all mating sets of compression members will be needed for a patient. In some examples, the clinician may first mark out the location of the target vein (e.g., the GSV) on the skin of the patient with a surgical pen to aid in placing the compressive members and, in some examples, positioning the respective ribs.

FIG. 3 is a cross-sectional view of a limb 28 compressed by the compression members 42 and 44 of the example compression cuff 40. As shown in the example of FIG. 3, the lateral compression member 44A has been coupled to the medial compression member 42A by attachment elements 52A and 54A, respectively. The compression members 42A and 44A extend in opposite directions around the limb 28 from the central body 46. In the example shown in FIG. 3, the lateral compression member 44A overlaps the medial compression member 42A such that the attachment element 52A can contact the attachment element 54A and create the loop configuration for the pair of the compression members 42A and 44A. The lateral compression member 44A may overlap the medial compression member 42 to the extent needed to attach the attachment elements 52A and 54A. More overlapping may result in a smaller circumference of the loop configuration. This loop configuration can be created with an appropriate circumference that applies the desired compression to a portion of the limb 28.

In the example shown in FIG. 3, a rib structure 50A is positioned on a radially inward facing surface of the medial compression member 42A (when the medial compression member 42A and lateral compression member 44A are connected to define the loop configuration) in order to focus the compression pressure applied to the limb 28 by the rib structure 50A. This pressure applied by the rib structure 50A may result in a more targeted collapse of the portion of the vein 20 beneath the rib structure 50A, thereby potentially lessening the overall pressure needed to be applied to the limb 28. Collapse of the portion of the vein 20 provides an occlusion against which the adhesive may be delivered, or provides compression to enable coapting the walls of the vein 20 with the bolus of adhesive delivered to the target location within the vein 20. In some examples, the rib structure 50A may be configured to be moved laterally (e.g., along the length of the respective compression member away from or towards the central body 46) on the radially inward facing surface 48 to facilitate placement of the rib structure 50A directly over the vein 20. For example, the hollow anatomical structure, e.g., the greater saphenous vein, may turn medially or laterally as it runs through the leg instead of creating a straight line. Therefore, the clinician may desire to move the rib structures with respect to the respective medial compression member 42 in order to appropriately place the rib structure directly above the actual position of the vein. The rib structures 50 may be attached to the medial compression members 42 in any manner that enables the rib structure 50 to be moved along a length of the medial compression member 42. For example, the rib structures 50 may be attached to the medial compression members 42 by hook and loop fasteners. In another example, the rib structures 50 may include an slot arranged in a circumferential direction through which the medial compression member 42 passes, enabling the rib structures 50 to slide along the length of the medial compression member (e.g., laterally or medially) to arrive at the location of the target vein.

Figure 4:
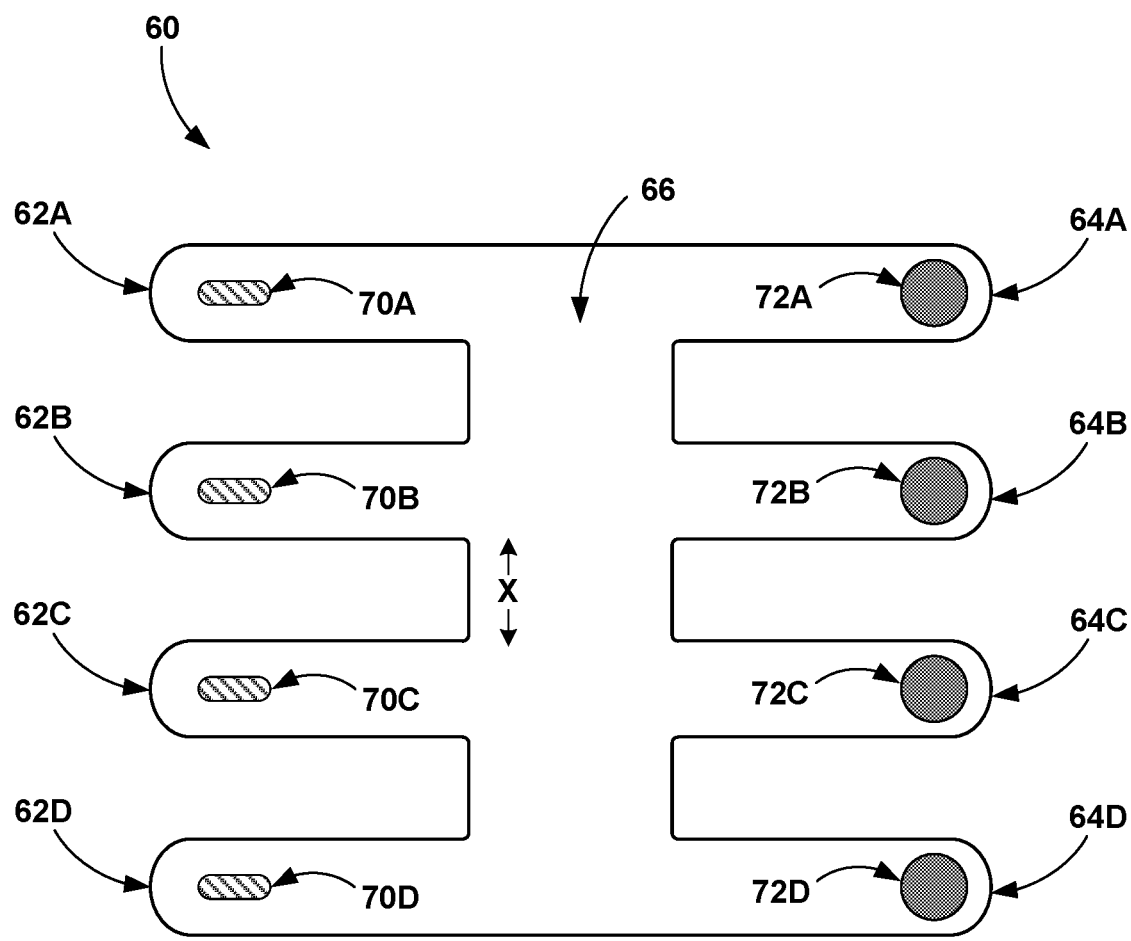
FIG. 4 is a bottom view of an example compression cuff having spacing between each compression member.

FIG. 4 is a bottom view of an example compression cuff 60 having a distance X between each compression member on each side of the compression cuff 60. The compression cuff 60 is similar to the compression cuff 40 of FIGS. 1A-1C. However, the compression cuff 60 may include larger gaps between adjacent compression members than the example of the compression cuff 40 shown in FIG. 1A. As shown in FIG. 4, the compression cuff 60 includes medial compression members 62A, 62B, 62C, and 62D (collectively "the medial compression members 62"), lateral compression members 64A, 64B, 64C, and 64D (collectively "the lateral compression members 64"), a central body 66, rib structures 70A, 70B, 70C, and 70D (collectively "the rib structures 70"), and attachment elements 72A, 72B, 72C, and 72D (collectively "the attachment elements 72"). The compression members 62 and 64 may be similar to the compression members 42 and 44, respectively, of the compression cuff 40. The central body 66 is similar to central body 46 of the compression cuff 40, the rib structures 70 are similar to the rib structures 50 of compression cuff 40, and the attachment elements 72 are similar to attachment elements 52 of compression cuff 40.

The compression cuff 60 includes the compression members 62 and 64 spaced apart from each other by a distance X. The distance X may be selected to correspond to the distance between target locations at which the clinician will inject adhesive into the hollow anatomical structure to be treated. In other words, when the delivered boluses of adhesive are spaced out within the hollow anatomical structure, the compression cuff 60 does not need to provide compression at those locations in between the target locations that will include the boluses of adhesive. In some examples, adjacent medial compression members 62 are separated from each other by a distance from approximately 0.5 cm to approximately 6.5 cm, and adjacent lateral compression members 64 are separated from each other by a distance from approximately 0.5 cm to approximately 6.5 cm. In other examples, the medial compression members 62 are separated from each other by a distance from approximately 3 cm to approximately 5 cm, and the lateral compression members 64 are separated from each other by a distance from approximately 3 cm to approximately 5 cm.

In some examples, the distance X is the same for the compression cuff 60. In other examples, the distance X may be different between different compression members. For example, the distance X between the medial compression members 62A and 62B may be less than the distance between the lateral compression members 62C and 62D. In this manner, the distance X between the compression members 62 and 64 may vary along the longitudinal direction of the compression cuff 60. In other examples, two or more of the compression members 62 and/or 64 may at least partially overlap. In this manner, the distance between adjacent compression members 62 and 64 may be selected according to the particular hollow anatomical structure to be treated or the specific procedure for delivering the adhesive to the patient.

Figure 5:
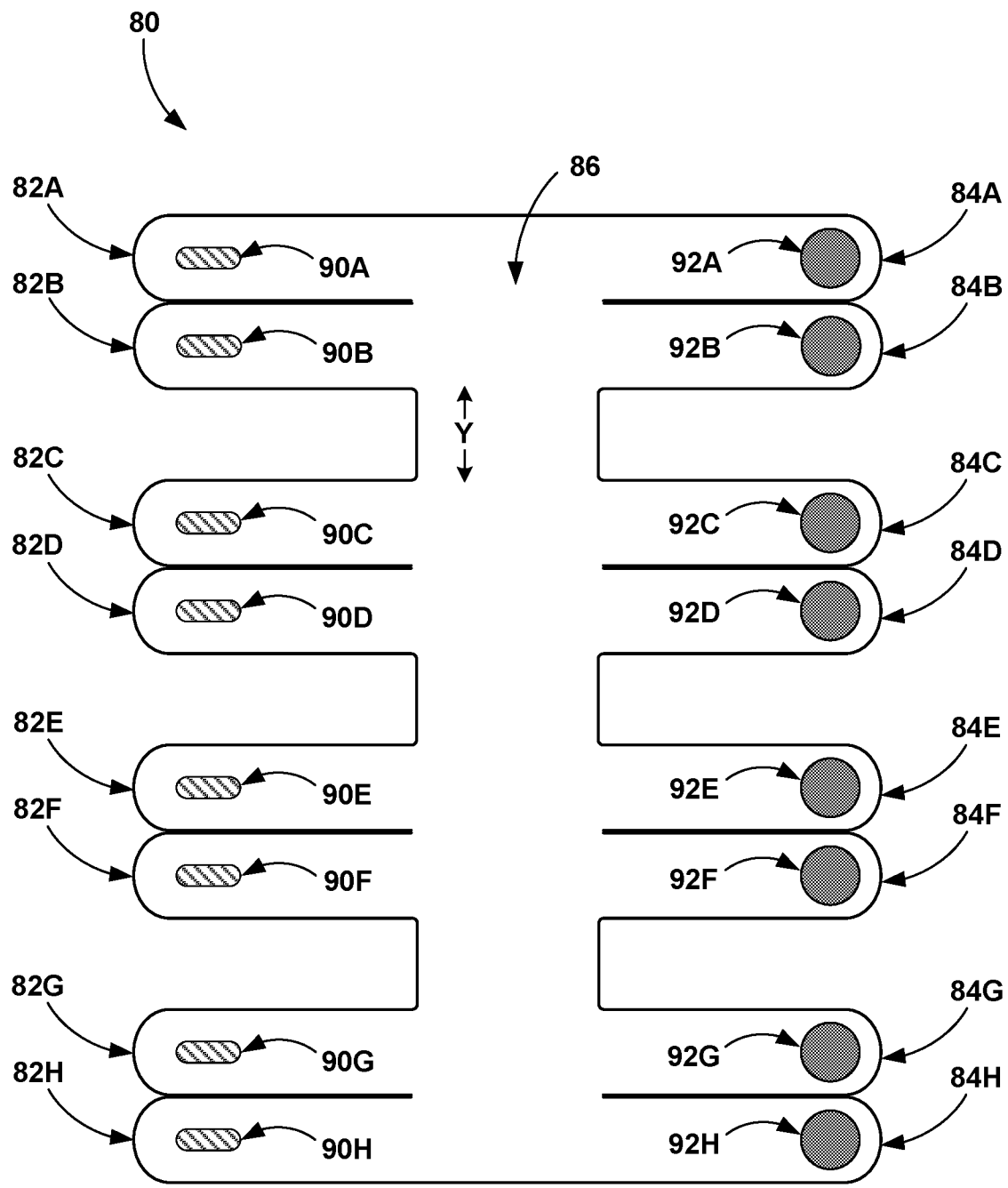
FIG. 5 is a bottom view of an example compression cuff having spacing between pairs of compression members.

FIG. 5 is a bottom view of an example compression cuff 80 having a distance Y between adjacent sets (e.g., pairs) of compression members. The compression cuff 80 is similar to the compression cuff 40 of FIGS. 1A-1C. However, the compression cuff 80 may include gaps between sets of adjacent compression members. As shown in FIG. 5, the compression cuff 80 includes medial compression members 82A, 82B, 82C, 82D, 82E, 82F, 82G, 82H (collectively "the medial compression members 82"), lateral compression members 84A, 84B, 84C, 84D, 84E, 84F, 84G, 84H (collectively "the lateral compression members 84"), a central body 86, rib structures 90A, 90B, 90C, 90D, 90E, 90F, 90G, 90H (collectively "the rib structures 90"), and attachment elements 92A, 92B, 92C, 92D, 92E, 92F, 92G, 92H (collectively "the attachment elements 92"). The compression members 82 and 84 are similar to the compression members 42 and 44, respectively, of the compression cuff 40. The central body 86 is similar to central body 46 of the compression cuff 40, the rib structures 90 are similar to the rib structures 50 of compression cuff 40, and the attachment elements 92 are similar to attachment elements 52 of compression cuff 40.

The compression cuff 80 includes pairs of the compression members 82 and 84 spaced apart from each other by a distance Y. In other words, a gap of distance Y is provided between every other of the compression members 82 and 84, where the gap between other compression members is relatively small or not present. For example, a gap of the distance Y is present between the pair of the medial compression members 82A and 82B and the pair of the lateral compression members 82C and 82D. The first set of compression members 82 and 84 in the pair are configured to compress and occlude the hollow anatomical structure and the second set of compression members 82 and 84 in the pair are configured to compress and coapt the walls of the hollow anatomical structure with injected adhesive. For example, the compression members 82A and 84A are attached to create a loop configuration and create an occlusion in a vein. Then, after a bolus of adhesive is injected into the vein and adjacent to the occlusion, the clinician creates a loop configuration with the compression members 82B and 84B. The next occlusion can then be made with the compression members 82C and 84C at a distance Y from the injected bolus of adhesive. This process can continue along the rest of the length of the compression cuff 80.

The distance Y may be selected to correspond to the distance between target locations at which the clinician will inject adhesive into the hollow anatomical structure to be treated and the next occlusion is to be created with the compression cuff 80. In other words, when the delivered boluses of adhesive are spaced out within the hollow anatomical structure, the compression cuff 80 does not need to provide compression at those locations in between the target locations that will include the boluses of adhesive. In some examples, the pairs of medial compression members 82 are separated from each other by a distance from approximately 0.5 cm to approximately 5.5 cm, and the pairs of the lateral compression members 84 are separated from each other by a distance from approximately 0.5 cm to approximately 5.5 cm. In other examples, the pairs of the medial compression members 82 are separated from each other by a distance from approximately 2 cm to approximately 4 cm, and the pairs of the lateral compression members 84 are separated from each other by a distance from approximately 2 cm to approximately 4 cm.

The distance Y may be different between different pairs of compression members. For example, the distance Y between the medial compression members 82B and 82C may be less than the distance between the medial compression members 82F and 82G. In this manner, the distance Y between the compression members 82 and 84 may vary along the longitudinal direction of the compression cuff 80. In other examples, two or more of the compression members 82 and/or 84 that are in pairs may at least partially overlap. In this manner, the distance between adjacent compression members 82 and 84 may be selected according to the particular hollow anatomical structure to be treated or the specific procedure for delivering the adhesive to the patient.

Figure 6:
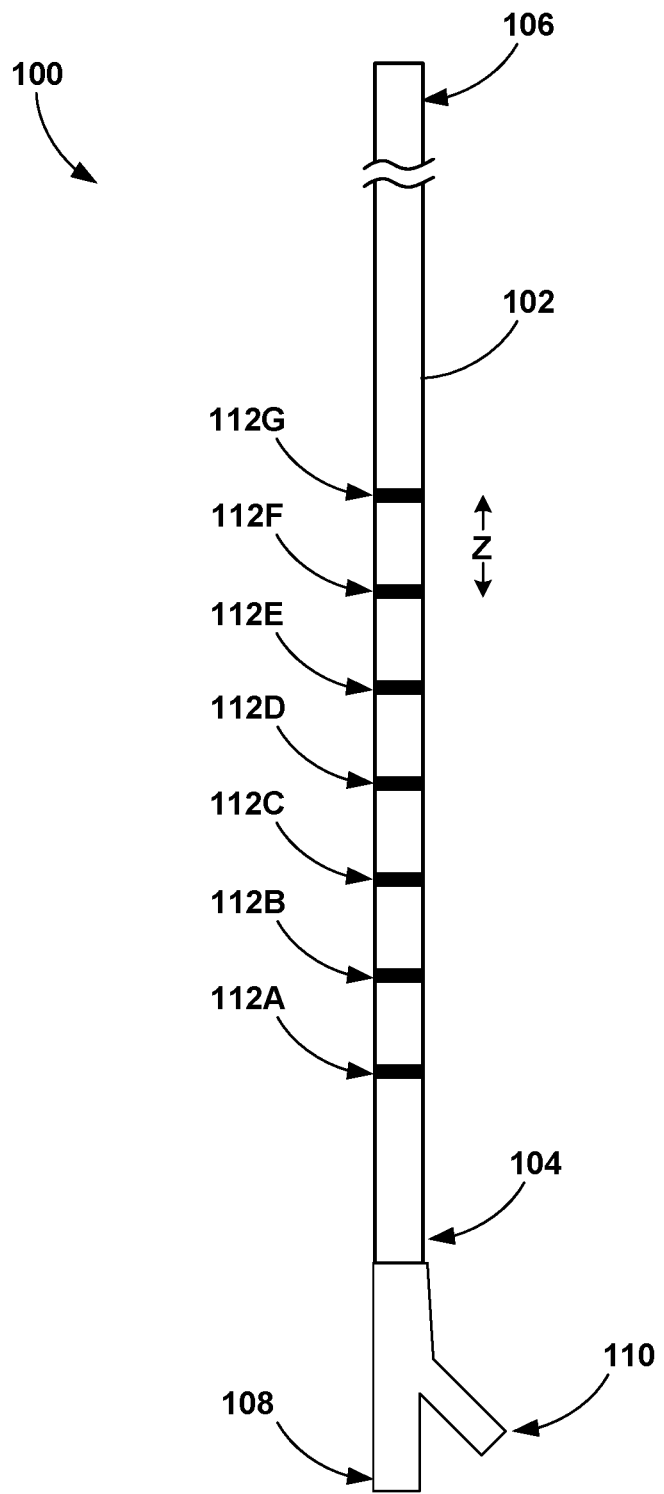
FIG. 6 is a side view of an example catheter having external markings with a marking spacing that corresponds to the spacing of compression members of a compression cuff.

FIG. 6 is a side view of an example catheter 100 having external markings with a marking spacing that corresponds to the spacing of compression members of a compression cuff. As shown in the example of FIG. 6, the catheter 100 is configured to deliver an adhesive material to a hollow anatomical structure, similar to catheter 12 of FIGS. 2A-2E. The catheter 100 includes an elongated member 102 that defines an inner lumen (not shown), a proximal end 104, and a distal end 106. Ports 108 and 110 enable devices or materials, such as the adhesive material and/or a guidewire, to be inserted into the inner lumen of the elongated member 102, and the adhesive material may be delivered out of the distal end 106. The elongated member 102 may be transparent, partially transparent, or opaque. The external markings 112 may be disposed on the outside of the elongated member 102 or otherwise visible and may be formed by ink, paint, or other coating, by etchings, detents, or any other type of visible and/or structural feature. In some examples, a structural feature, e.g., a detent, may provide a tactile indication to the clinician during withdrawal of the catheter 100 that indicates the external marking 112 has exited the introducer sheath and the distal end 106 is at the next target location for the adhesive.

The catheter 100 defines a lumen through which an adhesive material can be delivered to a hollow anatomical structure within the limb, such as a vein. The catheter 100 includes a plurality of external markings 112A, 112B, 112C, 112D, 112E, 112F, 112G (collectively "the external markings 112"). Adjacent external markings 112 have a marking spacing Z that corresponds to a spacing between adjacent compression members of a compression cuff, such as the compression cuff 40. During a medical procedure, the catheter 100 may be disposed within an introducer sheath (not shown). When the catheter 100 is withdrawn with respect to the introducer sheath, the next external marking 112 that exits a proximal end of the introducer sheath to be visible indicates that the distal end 106 of the catheter 100 is at the next target location within the hollow anatomical structure.

In one example, the spacing Z between adjacent markings 112 may correspond to the distance between the midline of the medial compression members 42A and 42B of the compression cuff 40. In this manner, the spacing Z may indicate the distance between consecutive boluses to be injected into the hollow anatomical structure. Therefore, markings 112 enable the rib structures 50 to be correctly positioned to apply pressure to the hollow anatomical structure at the target location at which the bolus of adhesive was delivered without requiring the clinician to measure how far to withdraw the catheter 100 for each next target location. In some examples, the marking spacing Z of the plurality of external markings 112 is from approximately 1.0 cm to approximately 7.0 cm. The marking spacing Z, and the number of external markings 112, may be selected to correspond to the type of compression cuff used, such as any of the compression cuffs 40, 60, or 80 described herein. In other embodiments, such as when medial compression member 42A is used to create an occlusion against which a bolus of adhesive is placed, and medial compression member 42B is used to coapt the hollow anatomical structure with the adhesive, the clinician may withdraw the catheter two markings 112 such that the distal tip 106 of the catheter 100 is at the proper target location.

Figure 7:
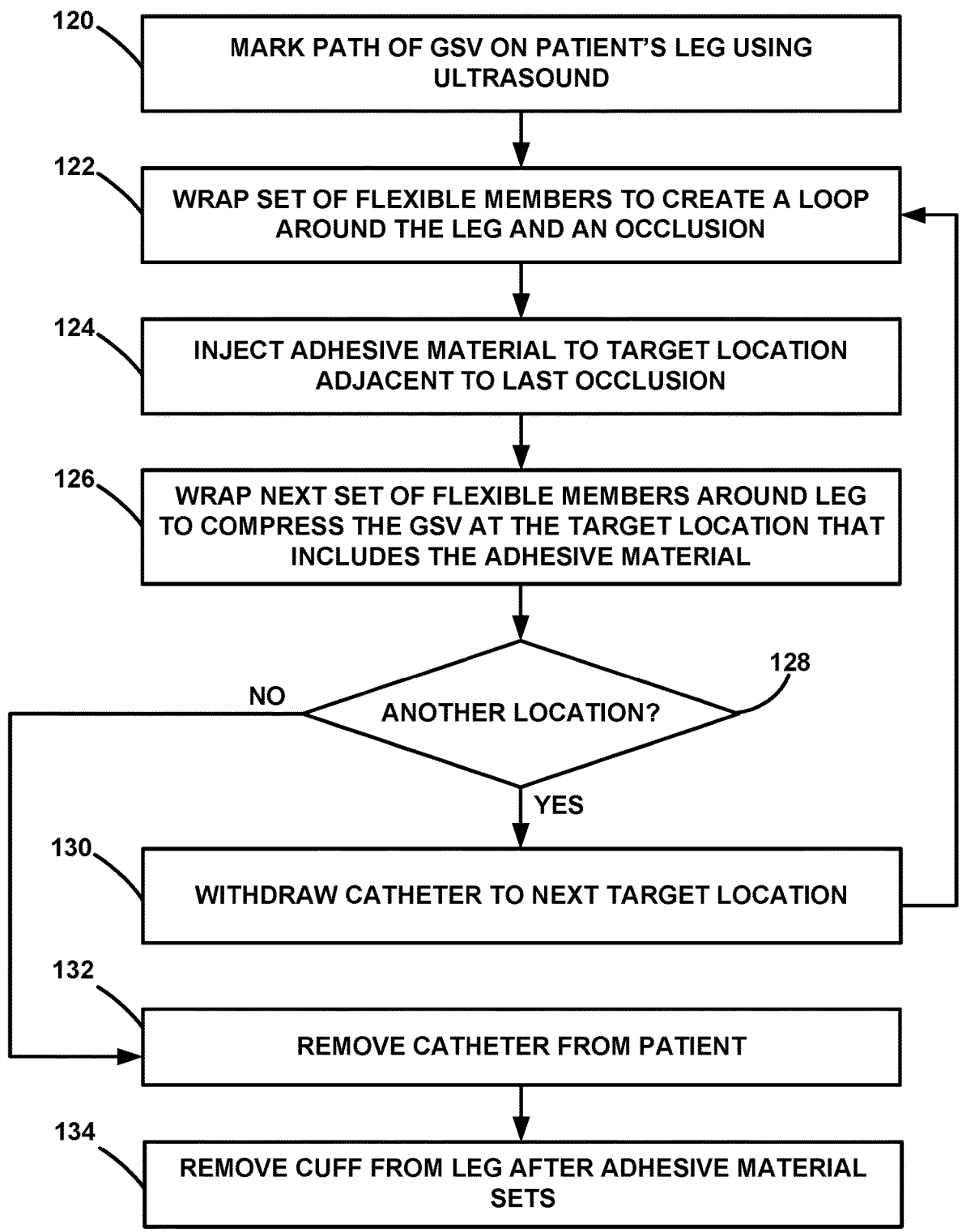
FIG. 7 is a flow diagram of an example technique for injecting an adhesive material into a hollow anatomical structure and wrapping compression members of a compression cuff around the limb to coapt the walls of the hollow anatomical structure with the adhesive material.

FIG. 7 is a flow diagram of an example technique for injecting an adhesive material into a hollow anatomical structure and wrapping the compression members 42 and 44 of the compression cuff 40 around the limb to coapt the walls of the hollow anatomical structure with the adhesive material. For illustrative purposes, the techniques of FIG. 7 are described with reference to the various aspects of the compression cuff 40 of FIGS. 1A-3E. However, such descriptions are not intended to be limiting and the techniques of FIG. 7 may be used with other devices or systems, such as the compression cuffs 60 or 80 in other examples.

As shown in the example of FIG. 7, a clinician may use an ultrasound transducer (e.g., ultrasound transducer 16 of FIG. 2A) to identify the greater saphenous vein (GSV) within the leg of the patient and then mark the path of the GSV on the skin of the patient (120). For example, the clinician may use a marker to create a visual marking of the path of the GSV underneath the skin. Next, the clinician may place the compression cuff 40 under the leg of the patient and then wrap a set of the compression members 42 and 44 (e.g., the compression members 42A and 44A) around the leg and attach the attachment elements 52 and 54 (e.g., attachment elements 52A and 54A) to create a loop configuration that results in an occlusion in the GSV (122). This target location of the occlusion may be selected to be proximal from the junction between the GSV and femoral vein, in one example. The rib structure 50A helps provide the pressure to the skin that results in the closure, and occlusion, of the GSV from the compression members 42A and 44B. The first occlusion created in the GSV by the compression cuff 40 may reduce the amount of, or prevent, adhesive in the first bolus from migrating downstream (i.e., towards the heart) in the GSV.

Next, the clinician may place the distal end 14B of the catheter 12 at the target location adjacent the occlusion and then inject a bolus of the adhesive material to the target location (124). In some examples, the bolus of the adhesive material may be injected against the occlusion and contact the occlusion. Once the adhesive is injected against the occlusion, the clinician wraps the next set of the compression members 42 and 44 (e.g., the compression members 42B and 44B) around the leg of the patient and attach the attachment elements 52 and 54 (e.g., attachment elements 52B and 54B) to create a loop configuration that results in compression of the walls of the GSV against the bolus of adhesive injected into the GSV, thereby coapting the vein closed (126). If there is another target location to be treated with the adhesive ("YES" branch of FIG. 7), the clinician may withdraw the catheter 12 to the next target location (130) and then create another occlusion by wrapping the next set of compression members 42 and 44 around the leg of the patient (122), another bolus of adhesive is injected against that formed occlusion (124), and the next set of compression members 42 and 44 are wrapped around the leg of the patient to coapt the vein closed (126). In some examples, a catheter such as the catheter 100 may be used so that the clinician can use the external markings to determine the distance to withdraw the catheter 100.

If there is not another target location to be treated with the adhesive ("NO" branch of FIG. 7), the clinician may completely remove the catheter 12 from the patient (132). Then, after the delivered boluses of adhesive have had sufficient time to set and/or cure (e.g., polymerize), the clinician may remove the compression cuff 40 from the leg of the patient by detaching the medial compression members 42 from the respective lateral compression members 44 (134). In some examples, the clinician may remove some sets of compression members 42 and 44 from the leg before the end of the procedure if the amount of time to set the adhesive is less than the amount of time required to complete the procedure.

Various examples have been described. These and other examples are within the scope of the following claims.

What is claimed is:

1. A medical assembly configured to compress a portion of a limb of a patient, the medical assembly comprising:
   a central body;
   a plurality of medial compression members extending from the central body in a first direction, each medial compression member of the plurality of medial compression members comprising a first attachment element;
   a plurality of rib structures, wherein each rib structure of the plurality of rib structures is disposed on a respective medial compression member of the plurality of medial compression members; and
   a plurality of lateral compression members extending from the central body in a second direction different than the first direction, each lateral compression member of the plurality of lateral compression members comprising a second attachment element, wherein each first attachment element is configured to attach to the respective second attachment element to create a respective loop configuration with a respective medial compression member and lateral compression member pair to compress the portion of the limb of the patient, wherein each rib structure is disposed on the respective medial compression member such that each rib structure is directed in a radially inward facing direction in the loop configuration, and wherein each rib structure is configured to apply pressure against skin of the patient to compress a vein within the limb.

2. The medical assembly of claim 1, wherein the plurality of medial compression members and the plurality of lateral compression members are flexible in a lateral direction to form the respective loop configurations.

3. The medical assembly of claim 1, wherein the plurality of medial compression members comprises at least five medial compression members and the plurality of lateral compression members comprises at least five lateral compression members.

4. The medical assembly of claim 1, wherein the plurality of medial compression members are separated from each other by a distance less than approximately 0.5 centimeters (cm), and wherein the plurality of lateral compression members are separated from each other by a distance less than approximately 0.5 cm.

5. The medical assembly of claim 1, wherein the plurality of medial compression members are separated from each other by a distance from approximately 0.5 cm to approximately 6.5 cm, and wherein the plurality of lateral compression members are separated from each other by a distance from approximately 0.5 cm to approximately 6.5 cm.

6. The medical assembly of claim 1, wherein the plurality of medial compression members are arranged in pairs of medial compression members, each pair of medial compression members being separated from an adjacent pair of medial compression members by a distance from approximately 0.5 cm to approximately 6.5 cm, and wherein the plurality of lateral compression members are arranged in pairs of lateral compression members, each pair of lateral compression members being separated from an adjacent pair of lateral compression members by a distance from approximately 0.5 cm to approximately 6.5 cm.

7. The medical assembly of claim 1, wherein the plurality of medial compression members, the plurality of lateral compression members, and the central body form a unitary structure.

8. The medical assembly of claim 1, wherein each first attachment element comprises a plurality of loops and each second attachment element comprises a plurality of hooks, the plurality of hooks being configured to secure to the plurality of loops.

9. The medical assembly of claim 1, wherein each rib structure of the plurality of rib structures is attached to a surface of the respective medial compression member, the surface being a radially inward facing surface in the loop configuration.

10. The medical assembly of claim 9, wherein each rib structure of the plurality of rib structures comprises a cross-section having a quadrilateral shape.

11. The medical assembly of claim 9, wherein at least one rib structure of the plurality of rib structures is moveable to different locations on the surface of the respective medial compression member.

12. A medical system comprising:
a compression cuff configured to compress a portion of a limb of the patient, the compression cuff comprising:
a central body;
a plurality of medial compression members extending from the central body in a first direction, each medial compression member of the plurality of medial compression members comprising a first attachment element; and
a plurality of lateral compression members extending from the central body in a second direction different than the first direction, each lateral compression member of the plurality of lateral compression members comprising a second attachment element, wherein each first attachment element is configured to attach to the respective second attachment element to create a respective loop configuration with a respective medial compression member and lateral compression member pair to compress a portion of the limb of the patient; and
a catheter configured to deliver an adhesive material to a hollow anatomical structure within the limb, the catheter comprising a plurality of external markings, each external marking of the plurality of external markings being spaced from an adjacent external marking by a marking spacing that corresponds to a spacing between adjacent medial compression members of the plurality of medial compression members.

13. The medical system of claim 12, wherein the marking spacing is from approximately 1.0 cm to approximately 7.0 cm.

14. The medical system of claim 12, wherein the plurality of medial compression members, the plurality of lateral compression members, and the central body form a unitary structure.

15. The medical system of claim 12, further comprising a plurality of rib structures, wherein each rib structure of the plurality of rib structures is attached to a surface of a respective medial compression member, the surface being a radially inward facing surface in the loop configuration, and wherein the rib structure is configured to apply pressure against skin of the patient to compress the hollow anatomical structure within the limb.

16. A method for treating a hollow anatomical structure within a limb of a patient, the method comprising:
delivering, from a catheter inserted in the hollow anatomical structure, a first bolus of adhesive material to a first target location within the hollow anatomical structure;
wrapping a first set of compression members of a compression cuff around the limb to create a first loop configuration around and compressing a first portion of the limb that corresponds to the first target location, wherein:
the first set of compression members comprises one medial compression member of a plurality of medial compression members extending from a central body in a first direction and one lateral compression member of a plurality of lateral compression members extending from the central body in a second direction different than the first direction,
each medial compression member of the plurality of medial compression members comprises a first attachment element and a rib disposed on the respective medial compression member, wherein wrapping the first set of compression members comprises positioning each rib of the respective medial compression member over the hollow anatomical structure to compress a portion of the hollow anatomical structure, and
each lateral compression member of the plurality of lateral compression members comprises a second attachment element, each first attachment element being configured to attach to a respective second attachment element to create a respective loop configuration with a respective medial compression member and lateral compression member pair;
withdrawing the catheter a distance from the first target location to a second target location;
delivering, from the catheter inserted into the hollow anatomical structure, a second bolus of adhesive material to the second target location within the hollow anatomical structure; and
wrapping a second set of compression members of the compression cuff around the limb to create a second loop configuration around and compressing a second portion of the limb that corresponds to the second target location.

17. The method of claim 16, further comprising, prior to delivering the first bolus of adhesive material to the first target location, wrapping a primary set of compression members of the compression cuff around the limb to create a first occlusion of the hollow anatomical structure distal to the first target location, wherein:
the primary set of compression members comprises one medial compression member distal to the one medial compression member of the first set of compression members and one lateral compression member distal to the one lateral compression member of the first set of compression members, and
delivering the first bolus of adhesive material to the first target location comprises introducing the first bolus of adhesive material proximal to the first occlusion.

18. The method of claim 16, further comprising:
identifying a path of the hollow anatomical structure via ultrasound imaging; and marking the path on skin of the limb of the patient.

19. The method of claim 16, wherein the catheter comprises a plurality of external markings, each external marking of the plurality of markings being spaced from an adjacent external marking by a marking spacing that corresponds to a spacing between each medial compression member of the plurality of medial compression members, and wherein withdrawing the catheter the distance from the first target location to the second target location comprises withdrawing the catheter until a next external marking is exposed from a proximal end of an introducer sheath.

20. The method of claim 16, further comprising removing the compression cuff from the limb of the patient after the adhesive material injected into the hollow anatomical structure has at least one of set or cured.

* * * * *